US010428278B2

(12) United States Patent
Snell

(10) Patent No.: US 10,428,278 B2
(45) Date of Patent: Oct. 1, 2019

(54) METHOD AND SYSTEM FOR PRODUCING AROMATIC HYDROCARBONS FROM A RENEWABLE RESOURCE

(71) Applicant: Chevron Phillips Chemical Company LP, The Woodlands, TX (US)

(72) Inventor: Ryan W. Snell, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 15/623,935

(22) Filed: Jun. 15, 2017

(65) Prior Publication Data
US 2018/0362856 A1 Dec. 20, 2018

(51) Int. Cl.
| | | |
|---|---|---|
| *C10G 3/00* | (2006.01) | |
| *C10G 35/095* | (2006.01) | |
| *C07C 2/64* | (2006.01) | |
| *C07C 5/327* | (2006.01) | |
| *C07C 5/41* | (2006.01) | |
| *C07C 1/247* | (2006.01) | |
| *C07C 5/333* | (2006.01) | |
| *C01B 3/38* | (2006.01) | |

(52) U.S. Cl.
CPC ............ *C10G 3/52* (2013.01); *C01B 3/38* (2013.01); *C07C 1/247* (2013.01); *C07C 2/64* (2013.01); *C07C 5/327* (2013.01); *C07C 5/333* (2013.01); *C07C 5/417* (2013.01); *C10G 3/49* (2013.01); *C10G 35/095* (2013.01); *C01B 2203/0233* (2013.01); *C07C 2523/28* (2013.01); *C07C 2523/36* (2013.01); *C07C 2523/40* (2013.01); *C07C 2523/42* (2013.01); *C07C 2523/74* (2013.01); *C07C 2529/04* (2013.01); *C10G 2300/1011* (2013.01); *C10G 2300/202* (2013.01); *C10G 2400/30* (2013.01)

(58) Field of Classification Search
CPC ........... C07C 45/74; C07C 1/22; C07C 47/21; C07C 49/203; C07C 9/22; C10L 1/08; C10L 1/04; C10L 1/026; Y02P 30/20; Y02P 20/142; C10G 3/47; C10G 3/50; C10G 3/45; C10G 3/46; C10G 45/58; C10G 47/00

See application file for complete search history.

(56) References Cited

U.S. PATENT DOCUMENTS

| | | |
|---|---|---|
| 2,882,244 A | 4/1959 | Milton |
| 3,130,007 A | 4/1964 | Breck |
| 3,216,789 A | 11/1965 | Breck et al. |
| 4,021,447 A | 5/1977 | Rubin et al. |
| 4,503,023 A | 3/1985 | Breck et al. |
| 5,401,386 A | 3/1995 | Morrison et al. |
| 5,516,960 A | 5/1996 | Robinson |
| 5,877,367 A | 3/1999 | Witte |
| 5,879,838 A | 3/1999 | Lee |
| 6,004,452 A | 12/1999 | Ash et al. |
| 6,812,180 B2 | 11/2004 | Fukunaga |
| 7,153,801 B2 | 12/2006 | Wu |
| 7,932,425 B2 | 4/2011 | Blessing et al. |
| 8,362,310 B2 | 1/2013 | Blessing et al. |
| 8,569,555 B2 | 10/2013 | Blessing et al. |
| 8,742,183 B2 * | 6/2014 | McCall .................. C10G 45/02 44/308 |
| 2014/0066676 A1 | 3/2014 | Cheung |
| 2016/0272665 A1 * | 9/2016 | Delgass .................. C07C 2/864 |
| 2017/0128920 A1 * | 5/2017 | Wu .......................... B01J 29/62 |

OTHER PUBLICATIONS

Beeck, et al., "Direct Catalytic Conversion of Cellulose to Liquid Straight-chain Alkanes," Energy & Environmental Science, 2014.
Liu, et al., "One-pot Conversion of Cellulose into n-Hexane over the IReOx/SiO2 Catalyst Combined with HZSM-5," ACS Sustainable Chemistry & Engineering, 2014, vol. 2, Issue 7, pp. 1819-1827.
"Software estimates chemical, physical properties," Chemical & Engineering News, 1985, vol. 63, Issue 5, p. 27.
http://finance.yahoo.com/news/favorable-feedstock-costs-drop-cellulosic-123000903.html.

* cited by examiner

*Primary Examiner* — Sharon Pregler
(74) *Attorney, Agent, or Firm* — Eversheds Sutherland (US) LLP

(57) ABSTRACT

Disclosed are a method and a system for producing bio-derived aromatic hydrocarbons from a renewable resource. More particularly, the disclosure provides for the co-location of a biomass reactor unit and an aromatization reactor unit to produce benzene from a renewable source such as plant mass. Hexane produced from cellulose in the biomass reactor unit can be converted to benzene in the aromatization reactor unit and hydrogen produced in the aromatization reactor unit can be used in the biomass reactor unit. Also described is the use of a mixture of bio-derived hexane produced from cellulose and naphtha in an aromatization process.

25 Claims, 3 Drawing Sheets

METHOD AND SYSTEM FOR PRODUCING AROMATIC HYDROCARBONS FROM A RENEWABLE RESOURCE

CROSS REFERENCE TO RELATED APPLICATIONS

None.

TECHNICAL FIELD

The present disclosure is directed to a method and system for producing aromatic hydrocarbons such as benzene from a renewable resource.

BACKGROUND

The consumer market increasingly demands products that are bio-derived, sustainable or "green." This demand has resulted in a growing interest in processes for making products that are produced—at least in part—from a renewable resource, or products that include some form of post-consumer recycled material, or perhaps offer improved recycling pathways.

Many commercially important polymers such as polystyrenes, polyesters, and nylons have come to be perceived negatively by consumers because they are conventionally made from non-renewable, aromatic hydrocarbons. For example, polystyrene resins and copolymers are used, in the production of packaging, automotive parts, and insulated containers and have few recycling options. Likewise, polyesters such as polyethylene terephthalate are widely used in packaging, such as in water bottles and soft-drink bottles, and are also viewed negatively by consumers. The same consumer perception problem may apply to phenolic resins used in the production of coatings, and nylon which has many applications including packaging, which are also among the polymers that are produced from aromatic hydrocarbons.

Presently, aromatic hydrocarbons are almost entirely produced from petroleum distillates, particularly naphtha, and are therefore not renewably sourced. Thus, there remain significant challenges to producing aromatic hydrocarbons, and the polymers and products produced therefrom, entirely or partially from bio-derived feedstocks. Even if a portion of the aromatic hydrocarbon feedstock used to make the polymers could be sourced from a renewable, bio-derived material, much of the consumer perception problem could be addressed.

SUMMARY

Aromatization is the process for the conversion of aliphatic hydrocarbons found in a naphtha stream to aromatic hydrocarbons. Aromatization refers not to one, but to several reactions that take place simultaneously. These reactions include removal of hydrogen from cycloalkanes and alkyl-cycloalkanes, removal of hydrogen from and isomerization of alkyl-cycloalkanes, and removal of hydrogen from and cyclization of aliphatic hydrocarbons. Outside of these reactions, side reactions can occur, including dealkylation of alkylbenzenes, isomerization of aliphatic hydrocarbons, and hydrocracking reactions which produce light gaseous hydrocarbons such as methane, ethane, propane and butane.

These aromatic hydrocarbons, especially benzene, toluene, and xylenes, are valued as chemical precursors to polymer products, but they can also be valuable as solvents, and as fuel or fuel additives due to their high octane number. Given their commercial importance, an ongoing need exists for improved systems and processes designed to maximize the production of these aromatic hydrocarbons from sustainable or renewable materials.

In an aspect, this disclosure provides a system and method for producing paraffinic, naphthenic, olefinic hydrocarbons or mixtures thereof produced from cellulose and other biological feedstocks. These hydrocarbons form the basis for a bio-derived and therefore renewable feed stream to an aromatization reactor. In a further aspect, this disclosure provides a system and method for producing bio-derived feedstocks containing hexane from cellulose and other biological feedstocks which forms the basis for a bio-derived and therefore renewable feed stream to an aromatization reactor. This disclosure also provides the ability to use either petroleum-based or bio-derived feedstocks in a flexible manner depending on availability and costs, and to combine or blend the two, to provide a portion of the benzene from bio-derived sources. In another aspect, the system and process as described herein co-locates a biomass hydrodeoxygenation reactor and an aromatization reactor so that the biomass hydrodeoxygenation reactor can use hydrogen generated by the aromatization process to produce bio-derived feedstocks containing hexane and the aromatization reactor can use the bio-derived feedstocks produced by the hydrodeoxygenation plant as a feed stream in the production of bio-derived aromatic hydrocarbons.

Accordingly, one aspect of this disclosure provides a method for producing bio-derived aromatic hydrocarbons, the method comprising:

a) contacting a biomass with hydrogen in the presence of a hydrodeoxygenation catalyst in at least one hydrodeoxygenation reactor, under conditions that produce a bio-derived feedstock;

b) introducing the bio-derived feedstock into at least one aromatization reactor and contacting the bio-derived feedstock with an aromatization catalyst under conditions that produce aromatic hydrocarbons and hydrogen; and c) providing at least a portion of the hydrogen produced in the at least one aromatization reactor to the at least one hydrodeoxygenation reactor for contacting the biomass.

In this aspect, the hydrodeoxygenation reactor can be located proximate to the aromatization reactor, as defined herein.

A further aspect of this disclosure provides a reactor system for producing aromatic hydrocarbons comprising:

a) a first feed pipe for supplying a first feed stream comprising naphtha;

b) a second feed pipe for supplying a second feed stream comprising a bio-derived feedstock, in which the second feed pipe combines with the first feed pipe to form a reactant stream pipe;

c) a separations unit having an inlet and an outlet, situated in line with the first feed pipe, the second feed pipe, or the reactant stream pipe, configured to receive, respectively, the first feed stream, the second feed stream, or the reactant stream, and to discharge, respectively, a purified first feed stream, a purified second feed stream, or a purified reactant stream; and d) at least one aromatization reactor having an inlet to accept the reactant stream or the purified reactant stream, and further comprising an aromatization catalyst bed which converts at least a portion of the bio-derived feedstock to one or more aromatic hydrocarbons and hydrogen.

Also in this aspect, the hydrodeoxygenation reactor can be located proximate to the aromatization reactor to supply the second feed stream comprising a bio-derived feedstock to the second feed pipe.

One additional aspect provides a method for producing renewable styrene, the method comprising: contacting benzene with ethylene under conditions to produce ethylbenzene, wherein the benzene comprises at least about 10 wt. % bio-derived benzene; and dehydrogenating the ethylbenzene to produce a styrene product. For example, an aspect of the disclosure is a method for producing renewable styrene comprising:
 a) contacting a biomass with hydrogen in the presence of a hydrodeoxygenation catalyst in at least one hydrodeoxygenation reactor, under conditions that produce bio-derived feedstocks containing hexanes;
 b) introducing the bio-derived feedstocks in combination with a naphtha reactant stream into at least one aromatization reactor and contacting the bio-derived feedstocks and naphtha with an aromatization catalyst under conditions that produce benzene and hydrogen;
 c) providing at least a portion of the hydrogen produced in the at least one aromatization reactor to the at least one hydrodeoxygenation reactor for contacting the biomass;
 d) contacting the benzene with ethylene under conditions to produce ethylbenzene, wherein the benzene comprises at least about 10 wt. % bio-derived benzene; and
 e) dehydrogenating the ethylbenzene to produce a styrene product.

These and other aspects, embodiments and features are discussed in detail in the detailed description, the appended claims and the figures provided in this disclosure.

DETAILED DESCRIPTION

Definitions

Figure 1:
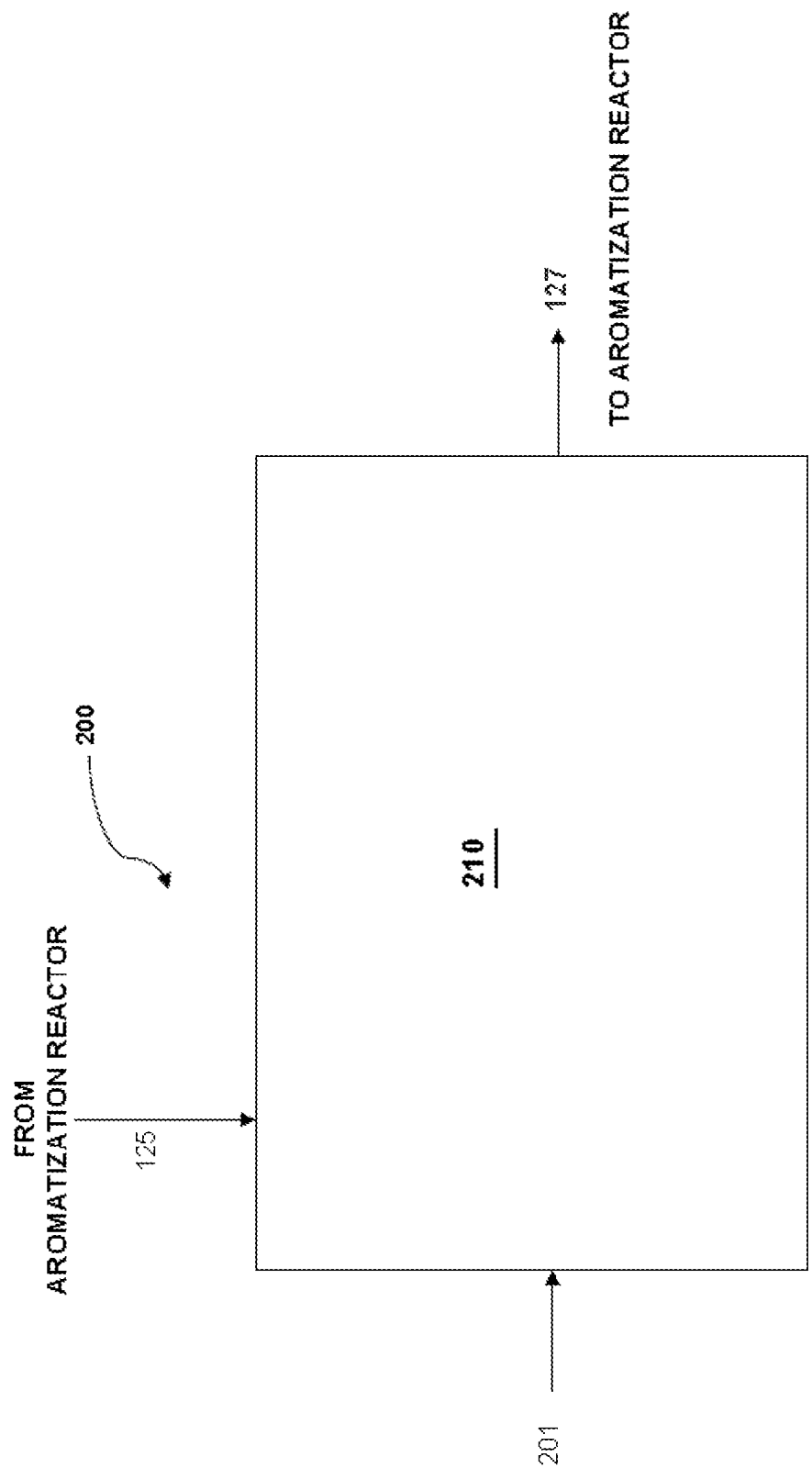
FIG. 1 presents a schematic diagram of an aspect of a biomass reactor system for use in the production of bio-derived feedstocks, which is sent to an aromatization reactor system for producing bio-derived aromatic hydrocarbons, and which receives hydrogen from the aromatization reactor system for the biomass reactor system.

Certain terms are used throughout the following description and claims to refer to particular features or components. As one skilled in the art will appreciate, different persons may refer to the same feature or component by different names. This document does not intend to exhaustively distinguish between components or features that differ in name but not structure or function.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), may be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

In the following discussion and in the claims, the terms "includes," "is," "containing," "having," "characterized by," and "comprises" are used in an open-ended fashion, and thus should be interpreted to mean "including, but not limited to." When systems and methods are claimed or described in terms of "comprising" various components or steps, the systems and methods can also "consist essentially of" or "consist of" the various components or steps, unless stated otherwise.

The terms "a," "an," and "the" are intended to include plural alternatives, for example, at least one. For instance, the disclosure of "a feedstock," "a compound," "a catalyst," and the like, is meant to encompass one, or mixtures or combinations of more than one feedstock, compound, catalyst, and the like, unless otherwise specified.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicants disclose, in an aspect of the invention, that one or more steps in the processes disclosed herein can be conducted at a temperature in a range from 65° C. to 75° C. This range should be interpreted as encompassing temperatures in a range from "about" 65° C. to "about" 75° C., and further encompass each of 65° C., 66° C., 67° C., 68° C., 69° C., 70° C., 71° C., 72° C., 73° C., 74° C., and 75° C., including any ranges and sub-ranges between any of these values.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants can be unaware of at the time of the filing of the application. Further, Applicants reserve the right to proviso out or exclude any individual substituents, groups, analogs, compounds, ligands, structures, pressures, temperatures, and the like, or any members of a claimed genus or subgenus, if for any reason Applicants choose to claim less than the full measure of the disclosure, for example, to account for a reference that Applicants can be unaware of at the time of the filing of the application.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

The following discussion is directed to various aspects or embodiments of the invention. The figures are not necessarily to scale, therefore, certain features of the embodiments may be shown exaggerated in scale or in somewhat schematic form and some details of conventional elements may not be shown in the interest of clarity and conciseness. Although one or more of these embodiments may be preferred, the embodiments disclosed should not be interpreted, or otherwise used, as limiting the scope of the disclosure, including the claims. It is to be fully recognized that the different teachings of the embodiments discussed below may be employed separately or in any suitable combination to produce desired results. In addition, one skilled in the art will understand that the following description has broad application, and the discussion of any embodiment is meant only to be exemplary of that embodiment, and not intended to intimate that the scope of the disclosure, including the claims, is limited to that embodiment.

As used herein, "about" is meant to account for variations due to measurement and/or experimental error. All numerical measurements are understood to be modified by the word "about", whether or not "about" is explicitly recited, unless specifically stated otherwise. Thus, for example, the statement "production of 10,000 tonnes," is understood to mean "production of about 10,000 tonnes."

Generally, groups of elements are indicated using the numbering scheme indicated in the version of the periodic table of elements published in Chemical and Engineering News, 63(5), 27, 1985. In some instances, a group of elements may be indicated using a common name assigned to the group; for example, alkali metals for Group 1 elements, alkaline earth metals for Group 2 elements, transition metals for Group 3-12 elements, halogens or halides for Group 17 elements, and the like.

For any particular compound or group disclosed herein, any name or structure (general or specific) presented is intended to encompass all conformational isomers, regioisomers, stereoisomers, and mixtures thereof that may arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For example, a general reference to hexane or hexanes includes n-hexane, 2-methylpentane, 3-methylpentane, 2,2-dimethylbutane, and 2,3-dimethylbutane; and a general reference to a butyl group includes an n-butyl group, a sec-butyl group, an iso-butyl group, and a t-butyl group.

In one aspect, a chemical "group" may be defined or described according to how that group is formally derived from a reference or "parent" compound, for example, by the number of hydrogen atoms removed from the parent compound to generate the group, even if that group is not literally synthesized in such a manner. These groups may be utilized as substituents or coordinated or bonded to metal atoms. By way of example, an "alkyl group" formally may be derived by removing one hydrogen atom from an alkane. The disclosure that a substituent, ligand, or other chemical moiety may constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

As used herein, the term "hydrocarbon" refers to a compound containing only carbon and hydrogen atoms. Other identifiers may be utilized to indicate the presence of particular groups, if any, in the hydrocarbon (for example, halogenated hydrocarbon indicates the presence of one or more halogen atoms replacing an equivalent number of hydrogen atoms in the hydrocarbon).

An "aromatic" compound or "aromatic hydrocarbon" is a compound containing a cyclically conjugated double bond system that follows the Hückel (4n+2) rule and contains (4n+2) pi-electrons, where n is an integer from 1 to 5. Aromatic hydrocarbons include "arenes" (aromatic compounds, for example, benzene, toluene, and xylenes) and "heteroarenes" (heteroaromatic compounds formally derived from arenes by replacement of one or more methine (—C=) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2)). As disclosed herein, the term "substituted" may be used to describe an aromatic group, arene, or heteroarene, wherein a non-hydrogen moiety formally replaces a hydrogen atom in the compound, and is intended to be non-limiting, unless specified otherwise.

As used herein, the term "alkane" refers to a saturated hydrocarbon compound. Other identifiers may be utilized to indicate the presence of particular groups, if any, in the alkane (for example, halogenated alkane indicates the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. The alkane or alkyl group may be linear or branched unless otherwise specified.

A "cycloalkane" is used herein to refer to a saturated cyclic hydrocarbon, with or without side chains, for example, cyclobutane, cyclopentane, cyclohexane, methyl cyclopentane, and methyl cyclohexane. Other identifiers may be utilized to indicate the presence of particular groups, if any, in the cycloalkane (for example, halogenated cycloalkane indicates the presence of one or more halogen atoms replacing an equivalent number of hydrogen atoms in the cycloalkane).

An "aliphatic" compound or "aliphatic hydrocarbon" is defined according to the IUPAC recommended definition to mean an acyclic or cyclic, saturated or unsaturated carbon compound, excluding aromatic compounds. That is, an aliphatic compound is a non-aromatic organic compound.

As used herein, a "paraffin" refers to a non-cyclic, linear or branched saturated hydrocarbons and includes alkanes. For example, a $C_6$ paraffin is a non-cyclic, linear or branched hydrocarbon having 6 carbon atoms per molecule. Normal hexane, methylpentanes, dimethylbutanes are examples of $C_6$ paraffins. A paraffin-containing feed comprises non-cyclic saturated hydrocarbons, such as normal paraffins, isoparaffins, and mixtures thereof.

As used herein, a "naphthene" and "naphthenic" are terms used to describe cyclic saturated hydrocarbons, and includes cycloalkanes and their alkyl-substituted analogs. Therefore, a "naphthene" is a cyclic, saturated hydrocarbon having one or more rings of carbon atoms in its chemical structure and is used herein to mean the same as "cycloalkane." If such a cyclic structure includes unsaturated carbon-carbon bonds but is not aromatic, such compounds would be aliphatic, but not naphthenic. In some embodiments, a naphthene is a cyclic, saturated hydrocarbon having from 5 to 8 carbon atoms in the cyclic structure, including substituted (particularly alkyl-substituted) analogs thereof.

As used herein, "olefin" is a acyclic or cyclic hydrocarbon having one or more carbon-carbon double bonds, apart from the formal ones in aromatic compounds. Olefins include alkenes, cycloalkenes, and corresponding polyenes.

As used herein, "naphtha" is a petroleum distillate fraction boiling within the range of from 50° F. (10° C.) to 550° F. (260° C.). In some embodiments, naphtha boils within the range of 70° F. (21° C.) to 450° F. (232° C.), and more typically within the range of 80° F. 27° C.) to 400° F. (2014° C.), and often within the range of 90° F. (32° C.) to 360° F. (182° C.). In some embodiments, at least 85 vol. % (volume percent) of naphtha boils within the range of from 50° F. (10° C.) to 550° F. (260° C.), and more typically within the range of from 70° F. (21° C.) to 450° F. (232° C.). In embodiments, at least 85 vol. % of naphtha is in the C4 to C12 range, and more typically in the C5 to C11 range, and often in the C6 to C10 range. Naphtha can include, for example, straight run naphthas, paraffinic and naphthenic raffinates from aromatic extraction or adsorption, C6 to C10 paraffin and naphthene containing feeds, bio-derived naphtha, naphtha from hydrocarbon synthesis processes, including Fischer-Tropsch and methanol synthesis processes, as well as naphtha from other refinery processes, such as hydrocracking or conventional reforming.

As used herein, the term "convertible hydrocarbon", "convertible $C_6$ species" or "convertible $C_7$ species" refers to hydrocarbon compounds that may be selectively converted to aromatic products such as aromatic hydrocarbons under aromatization process conditions. In some aspects, the feed stream comprises a highly branched hydrocarbon that is not selectively converted to aromatic hydrocarbons under conventional aromatization process conditions. While a "highly branched hydrocarbon" is a hydrocarbon that is not selectively convertible to form aromatic hydrocarbons under conventional aromatization process conditions. For example, a "highly branched hydrocarbon" can comprise highly-branched hydrocarbons having six or seven carbon atoms with an internal quaternary carbon or hydrocarbons having six carbons atoms and two adjacent internal tertiary carbons or mixtures thereof. The highly branched hydrocarbons may include, but are not limited to, dimethylbutanes (for example, 2,2-dimethylbutane, 2,3-dimethylbutane), dimethylpentanes (for example, 2,2-dimethylpentane, 3,3-dimethylpentane), trimethylbutanes (for example, 2,2,3-trimethylbutane) and mixtures thereof. The highly branched hydrocarbons are selectively convertible aromatic hydrocarbons and instead convert to light hydrocarbons under aromatization process conditions. The convertible components may comprise methylpentanes, methylhexanes, dimethylpentanes or mixtures thereof, and/or the selectively convertible components may comprise at least one of 2-methylpentane, 3-methylpentane, 2,4-dimethylpentane, 2,3-dimethylpentane, n-hexane, 2-methylhexane, 3-methylhexane, n-heptane, or mixtures thereof. The selectively convertible components readily convert to aromatic hydrocarbons without the production of light hydrocarbons.

As used herein "primary aromatic hydrocarbon," "primary aromatic product," "desired hydrocarbon product," and "particular aromatic species" are used interchangeably and refer to the aromatic hydrocarbons that is the desired end product of the reaction and comprises aromatic hydrocarbons that has been generated from a feed that includes a renewable cellulose source. For example, the desired product may be benzene while toluene and xylenes may be by-products, or the desired product may be xylenes while benzene and toluene may be by-products.

A "Group 8-10" metal includes each of the Group 8 metals iron, ruthenium and osmium, each of the Group 9 metals cobalt, rhodium and iridium, and each of the Group 10 metals nickel, palladium and platinum. The Group 8-10 metals may also be referred to using the earlier nomenclature, the Group VIII metals, which also encompasses all of iron, ruthenium, osmium, cobalt, rhodium, iridium, nickel, palladium and platinum. Generally, describing the catalyst as a Group 8-10 metal catalyst or as comprising a Group 8-10 metal, is intended to encompass catalysts that include at least one Group 8-10 metal and optionally other metals, such as Pt/Sn and Pt/Re.

As used herein "HDO plant," "HDO reactor," "HDO reactor unit," "hydrodeoxygenation plant," "hydrodeoxygenation reactor," "biomass plant," "biomass reactor unit" and the like are used interchangeably and refer to known reactor systems used to generate bio-derived feedstocks comprising or containing paraffinic hydrocarbons, naphthenic hydrocarbons, and typically olefinic hydrocarbons from, for example, a cellulose, a sugar, a starch, a lignocellulose, a hemicellulose, or a lignin, as appreciated by the person of ordinary skill. Thus, "hydrodeoxygenation" or "HDO" is understood by the skilled person to be a hydrogenolysis process for removing oxygen atoms from oxygen containing compounds such as carbohydrates by cleaving carbon-carbon and carbon-oxygen bonds, to form a paraffinic hydrocarbons and naphthenic hydrocarbons and water. Hydrodeoxygenation is usually carried out catalytically and encompasses a number of reactions.

As used herein a "bio-derived feedstock" refers to a mixture of paraffinic, naphthenic, and/or olefinic hydrocarbons that is produced from a renewable starting material such as cellulose. In an aspect, this disclosure provides a system and method for producing a bio-derived feedstock in a hydrodeoxygenation reactor from biological feedstocks as a feedstock for an aromatization reactor system. In a further aspect, this disclosure provides a system and method for producing a bio-derived feedstock containing hexane in a hydrodeoxygenation reactor from biological feedstocks for an aromatization reactor system.

As used herein to describe the relationship between the biomass reactor unit and aromatization reactor unit, "proximate" refers to the biomass reactor unit and aromatization unit operations being combined into an integrated process optionally with an integrated or common process control system. For example, process fluids, process gases, heat and co-products may be exchanged between the reactor units and/or other units of the HDO and aromatization processes. Additionally, the HDO and the aromatization unit operations may be, and may benefit from being, operated simultaneously. A proximate distance will, for example, be more efficient from an operational perspective; more economically feasible than operating an aromatization plant separate from an HDO plant as discrete and isolated processes, for example, over a distance of miles. Examples of efficiency achieved by a proximate distance include heat integration, byproduct recovery, labor utilization, and sharing of unit processes or unit control systems. A large proximate distance may, for example, involve achievement of these efficiencies through pipelines or facilities controlled or operated on behalf of the same party as the biomass reactor system, aromatization reactor system, or both; rather than via pipelines or facilities controlled or operated on behalf of third parties. A short proximate distance may, for example, involve achievement of these efficiencies between units with adjacent or even overlapping battery limits.

As used herein the term "aromatization reactor system," "aromatization reactor unit," "catalytic reactor system," and "catalytic reactor unit" when referring to aromatization reactor systems also refer to the reactor vessel, reactor internals, and associated processing equipment as the context allows, including but not limited to the catalyst, inert packing materials, scallops, flow distributors, center pipes, reactor ports, catalyst transfer and distribution system, furnaces and other heating devices, heat transfer equipment, and piping. The aromatization reactor system described may comprise a fixed catalyst bed system, a moving catalyst bed system, a fluidized catalyst bed system, or combinations thereof. Such aromatization reactor systems may be batch or continuous. In a fixed bed system, the flow of the feed can be upward, downward, or radially through the reactor.

As used herein "biomass" includes but is not limited to biological products comprising or selected from cellulose, monosaccharides, disaccharides, starch, hemicellulose, or lignin. Specific examples of biomass include cellulosic or lignocellulosic materials such as paper, paper products, paper waste, post-consumer recycled paper, wood, particle board, sawdust, agricultural waste, consumer waste, silage, grasses, rice hulls, bagasse, cotton, jute, hemp, flax, bamboo, sisal, abaca, straw, corn cobs, corn stover, switchgrass, alfalfa, hay, coconut hair, cotton, cassava, synthetic celluloses or mixtures of these. In some instances, biomass can be in solution, slurred, suspended, dry, frozen or mixtures thereof.

The term "halogen" has its usual meaning and, as the context allows, includes halides. Therefore, examples of halogens include fluorine, fluoride, chlorine, chloride, bromine, bromide, iodine, and iodide.

Molar selectivities are defined as follows:

Benzene selectivity: $S_{Bz} = \frac{\dot{n}_{Bz,prod}}{\dot{n}_{conv\ C6,feed} - \dot{n}_{conv\ C6,prod}}$ Eq. 1

Toluene selectivity: $S_{Tol} = \frac{\dot{n}_{Tol,prod}}{\dot{n}_{conv\ C7,feed} - \dot{n}_{conv\ C7,prod}}$ Eq. 2

Benzene+Toluene selectivity: $S_{Bz+Tol} = \frac{\dot{n}_{Bz,prod} + \dot{n}_{Tol,prod}}{\dot{n}_{conv\ C6,C7,feed} - \dot{n}_{conv\ C6,C7,prod}}$ Eq. 3

Aromatics selectivity: $S_{arom} = \frac{\dot{n}_{Bz,prod} + \dot{n}_{Tol,prod} + \dot{n}_{C8+arom,prod}}{\dot{n}_{conv\ C6-C8,feed} - \dot{n}_{conv\ C6-C8+,prod}}$ Eq. 4

Conversion is defined as the number of moles converted per mole of "convertible" hydrocarbons fed as follows:

C6 conversion: $X_{C6} = \frac{\dot{n}_{conv\ C6,feed} + \dot{n}_{conv\ C6,prod}}{\dot{n}_{conv\ C6,feed}}$ Eq. 5

C7 conversion: $X_{C7} = \frac{\dot{n}_{conv\ C7,feed} + \dot{n}_{conv\ C7,prod}}{\dot{n}_{conv\ C7,feed}}$ Eq. 6

C6+C7 conversion: $X_{C6+C7} = \frac{\dot{n}_{conv\ C6,feed} + \dot{n}_{conv\ C7,feed} - \dot{n}_{conv\ C6,prod} + \dot{n}_{conv\ C7,prod}}{\dot{n}_{conv\ C6,feed} + \dot{n}_{conv\ C7,feed}}$ Eq. 7

In these equations, $\dot{n}$ indicates a molar flow rate in a continuous reactor or the number of moles in a batch reactor.

A "tonne" is used herein to refer to a metric ton, that is, a unit of mass equal to 1,000 kilograms.

Description

This disclosure provides a system and method for producing bio-derived feedstocks containing paraffinic, naphthenic, and/or olefinic hydrocarbons (particularly hexane) from cellulose and other biological feedstocks which forms the basis for a bio-derived and therefore renewable feed stream to an aromatization reactor. The dehydrogenation of bio-derived feedstocks containing hexane is a reaction that results in a high yield of bio-derived aromatic hydrocarbons including benzene, for example, in a yield of greater than 80 wt. %. Typically, bio-derived feedstocks containing hexane production from cellulose is not as cost effective as the production of naphtha feedstock containing hexane from petroleum products, and therefore it is not generally used in the production of commercial aromatic hydrocarbons. However, this disclosure provides the benefits of at least the ability to use either petroleum-based or bio-derived feedstocks in a flexible manner depending on availability and costs, and to combine or blend bio-derived feedstocks containing hexane with naphtha or other petroleum-derived feeds to provide a portion of the aromatic hydrocarbons including benzene from bio-derived, and to enhance the consumer perception surrounding aromatic hydrocarbons and the polymers produced therefrom.

In one aspect, the system and process as described herein co-locates a biomass hydrodeoxygenation reactor unit for making bio-derived feedstocks containing paraffinic, naphthenic, and/or olefinic hydrocarbons (particularly hexane) from cellulose and an aromatization reactor unit to convert the bio-derived feedstocks to aromatic hydrocarbons including benzene in proximity of one another to take advantage of their synergies. More particularly, the system and method as described may co-locate the two reactor units so that the biomass hydrodeoxygenation reactor can use hydrogen generated by the aromatization process to produce the bio-derived feedstocks containing and the aromatization reactor can use the bio-derived feedstocks produced by the hydrodeoxygenation plant as a bio-derived feed stream in the production of bio-derived aromatic hydrocarbons.

Polymers produced from aromatic hydrocarbons are used in the production of a myriad of products. Finding sustainable or renewable reactants to generate polymeric materials is a desirable objective, but current systems for converting plant materials into fuels are generally not very efficient and require significant raw materials. The conversion of cellulose to bio-derived feedstocks containing hexane on a commercial scale is possible, however, the reaction requires significant amounts of hydrogen which is not easily stored or which must be produced separately from natural gas. For example, the necessary hydrogen can be provided by steam reforming natural gas, also known as steam methane reforming (SMR), a common method of producing hydrogen. SMR involves the reaction of methane with steam at high temperatures (from about 700° C. to about 1100° C.), typically in the presence of a metal-based catalyst, to produce carbon monoxide and hydrogen. Additional hydrogen can be recovered by reacting the carbon monoxide that is produced with steam, typically in the presence of a copper or iron catalyst, to produce carbon dioxide and hydrogen. Therefore, in some embodiments, waste gas from the hydrodeoxygenation reactor can include methane, which may be directed to a steam reformer reactor to produce hydrogen according to the method disclosed above, for use in the biomass reactor system.

In an aspect, a biomass reactor unit can be located proximate to an aromatization reactor unit in a plant, because the biomass reactor requires large amounts of hydrogen to convert oxygenated species such as cellulose or sugar (for example, glucose) to a bio-derived feedstock which includes hexane, and the aromatization reactor produces large amounts of hydrogen as a by-product of the aromatization reactions of petroleum based naphtha and bio-derived feedstock comprising paraffinic, naphthenic, and/or olefinic hydrocarbons including hexane. The hydrogen from the aromatization reactor can be used in the biomass reactor to produce bio-derived feedstocks containing hexane or other hydrocarbons, and the bio-derived feedstocks or other hydrocarbons can then be used as feedstock for the aromatization reactor.

The generation of the bio-derived feedstocks containing hexane from cellulose requires nearly two times more hydrogen, or more specifically 3 additional moles of $H_2$ than is released during the conversion of the same hexane to benzene assuming perfect conversion, as shown by the equations below.

$$C_6H_{14} \rightarrow C_6H_6 + 4H_2 \quad \text{Eq. 8}$$

$$C_6H_{12}O_6 + 7H_2 \rightarrow C_6H_{14} + 6H_2O \quad \text{Eq. 9}$$

Equation 8 depicts the reaction of the conversion of hexane to benzene, which, per mole of hexane converted, releases 4 moles of $H_2$. Equation 9 depicts the hydrodeoxygenation reaction of glucose with hydrogen to form hexane and water. As shown, to form hexane from glucose requires 7 moles of $H_2$ per mole of glucose.

Consideration of these reactions demonstrates the benefit gained by locating the biomass reactor system proximate to an aromatization reactor in a chemical plant. The bio-derived feedstocks containing hexane produced in the biomass reactor may be fed to an aromatization reactor that is already being used to convert petroleum-based aliphatic hydrocarbons to aromatic hydrocarbons. The resultant aromatic hydrocarbons product can include up to about 60 wt. % bio-derived aromatic hydrocarbons produced from the bio-derived feedstocks. One hundred percent by weight bio-derived aromatic hydrocarbons can be produced from bio-derived feedstocks, however, on the order of 75 wt. % more hydrogen will generally have to be introduced from a source beyond what can be generated by the aromatization reactor.

Aromatization plants are traditionally constructed within or near refineries, as the petroleum products comprising naphtha are readily available, and co-products from the aromatization plant have value to the refinery. As the described co-located reactors will continue to require petroleum based feedstock, these co-located reactors will generally be located proximate to a refinery. In some aspects, the co-located reactors may be controlled by a shared process control system.

Generally, the feedstock for the aromatization process is naphtha, a petroleum distillate which may be generated from crude oil, petroleum, natural condensates, or other suitable sources. The naphtha feedstock may comprise a light hydrocarbon, with a boiling range of about 20° C. to about 235° C. The naphtha feed contains a mixture of naphthenic, olefinic, and paraffinic hydrocarbons. While catalytic aromatization typically refers to the conversion of naphtha, other feedstocks also can be treated to provide product enriched in aromatic hydrocarbons. Therefore, in one aspect while the conversion of a bio-derived feedstock in the presence of naphtha is described, the present disclosure can be useful for the conversion or aromatization of bio-derived feedstocks with petroleum based naphtha feedstocks containing paraffinic hydrocarbons, olefinic hydrocarbons, naphthenic hydrocarbons, and mixtures thereof, and particularly saturated hydrocarbons. The particular aromatic hydrocarbons that are produced in the aromatization reactor(s) is dependent on the composition of the feedstock.

Typically, the naphtha feedstock is first fed into a purification process or purification module which is part of the aromatization reactor. The purification process employs known methods to purify the hydrocarbon feed, which may include fractionation, purification, treating or combinations thereof of the hydrocarbon feed. Fractionation may include removing heavy (for example, $C_9^+$) hydrocarbons, light (for example, $C_5^-$) hydrocarbons, or combinations thereof. Treating refers interchangeably to removing impurities, such as oxygenates, sulfur, metals or combinations thereof, from the hydrocarbon feed by catalytic and non-catalytic processes. Such treating processes include hydrotreating to remove sulfur over catalysts, and adsorption of impurities. The resulting purified stream, generally contains compounds with about 6 to about 9 carbon atoms, for example, about 6 to about 8 carbon atoms. Typically, for the production of a benzene product, the feedstock will have more $C_6$ compounds than $C_7$ to $C_8$ compounds, and generally will have substantially more $C_6$ compounds than $C_7$ to $C_8$ compounds. By "substantially" more, it is intended to reflect, for example, a 1.1- to 25-fold excess of $C_6$ compounds over $C_7$ to $C_8$ compounds, or alternatively, a 1.5- to 15-fold excess of $C_6$ compounds over $C_7$ to $C_8$ compounds. In any case, mixtures of aromatic compounds including benzene, toluene, and xylenes may be produced from available feedstocks.

FIG. 1 presents a schematic diagram of an aspect of a biomass reactor system for use in the production of bio-derived feedstocks containing hexane, which is sent to an aromatization reactor system for producing bio-derived aromatic hydrocarbons, and which receives hydrogen from the aromatization reactor for the biomass reactor system. Biomass reactor systems are well known and a number of methods, catalysts, and conditions are available for producing bio-derived feedstocks containing hexane from various biomass sources such as cellulosic feedstock. Examples of such methods and systems include, but are not limited to: [1] Op de Beeck, et al., Direct catalytic conversion of cellulose to liquid straight chain alkanes, Energy & Environmental Science, 2014 (DOI: 10.1039/c4ee01523a); and [2] Liu, et al., One-Pot Conversion of Cellulose into n-Hexane over the IR-ReO$_x$/SiO$_2$ Catalyst Combined with HZSM-5, ASC Sustainable Chem. Eng. 2014, 2, 1819-1827; each of which is incorporated herein in its entirety.

Referring to FIG. 1, biomass reactor system 200 can include at least one hydrodeoxygenation reactor 210 having a biomass feed stream 201 and a bio-derived feedstock stream 127. The biomass feed stream 201 comprises biomass including, for example, cellulose, lignin, hemi-cellulose, or combinations thereof. In one aspect, the cellulose may be fed to the hydrodeoxygenation reactor 210 without substantial purification. According to another aspect, prior to introduction of the cellulose to the hydrodeoxygenation reactor 210, the cellulose may be purified to remove impurities that may interfere with the hydrodeoxygenation reaction, including for example, nitrogen, sulfur, inorganic species or combinations thereof. In an aspect, the biomass may be concentrated prior to being fed into the hydrodeoxygenation reactor 210, by separating the cellulose from the remaining biomass, for example, removing lignin and hemicellulose. Increasing the cellulose content in the feed stream will result in improved yields of bio-derived feedstocks. Appropriate processes to remove impurities and/or to separate cellulose from the remaining biomass will be readily apparent to the skilled artisan.

Figure 2:
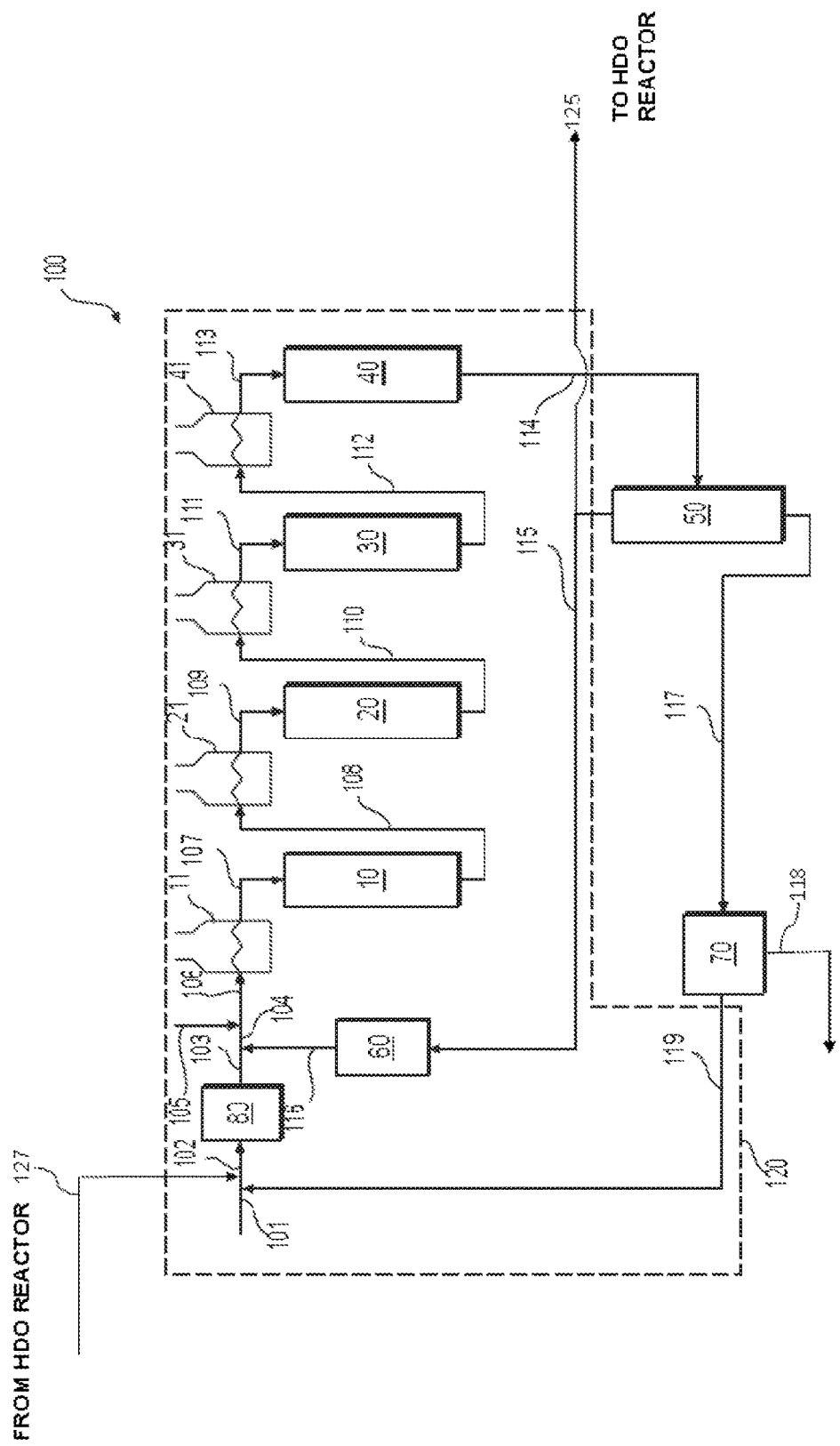
FIG. 2 presents a schematic diagram of an aspect of an aromatization reactor system for producing bio-derived aromatic hydrocarbons, in which a portion of the feed is a bio-derived feedstock produced from cellulose in a hydrodeoxygenation system. The hydrogen produced from the aromatization reactor is used in the biomass reactor system.

The biomass feed stream 201 comprising cellulose can be combined with hydrogen feed stream 125 from the aromatization reactor system 100, illustrated in FIG. 2. The cellulose is reacted with hydrogen in the presence of a catalyst, at a temperature and pressure sufficient to effect hydrodeoxygenation of the cellulose and the formation of the bio-derived feedstocks containing hexane. The at least one hydrodeoxygenation reactor 210 may be operated in a batch mode or continuously. In some embodiments, one or more of the biomass feed stream 201 comprising cellulose or the hydrogen feed stream 125 from the aromatization reactor system 100 may be pre-heated before being introduced to the at least one hydrodeoxygenation reactor 210. Generally, any suitable hydrotreating or hydrogenation/hydrodesulfurization catalyst can be used in the hydrodeoxygenation reaction as described, including but not limited to, those based on molybdenum, rhenium, iron, ruthenium, osmium, cobalt, rhodium, iridium, nickel, palladium, platinum, and further including catalysts such as Ir—Re supported catalysts and ZSM-5 zeolites. In some aspects of this disclosure, an acidic catalyst can be used to cleave cellulose bonds, such as ZSM-5, solid supports, or homogenous acids. In some aspects of the present invention, cellulose bonds are cleaved in two steps: a first step which cleaves glycosidic bonds and a second step which hydrodeoxygenates the cellulose. In some aspects, the hydrodeoxygenation reaction is carried out in the presence of a catalyst selected from those having metal hydrogenation and/or acidic active sites.

In aspects of the present disclosure, the hydrodeoxygenation process is carried out under the conditions specified for the particular biomass reactor system, method, catalyst, and the like, employed for this portion of the overall process. For example, the hydrodeoxygenation process can be carried out at a temperature of at least about 180° C., for example at least about 190° C., for example at least about 200° C., for example at least about 210° C., for example at least about 220° C., or for example at least about 230° C. A practical upper limit for the hydrodeoxygenation process temperature is about 350° C. and therefore the biomass reactor system can be carried out over any range between these temperatures. In aspects of the present disclosure, the hydrodeoxygenation process can be carried out at a pressure of from about 50 psig (344 KPa) to 2000 psig (13789 KPa), for example about 50 psig (344 KPa), about 500 psig (3447 KPa), about 1000 psig (6895 KPa), about 1500 psig (10342 KPa), about 200 psig (1379 KPa), and any ranges there between.

The literature reports a number of ways to produce bio-derived feedstocks containing hexane from cellulose, including multi-step processes and more recently, single step processes. Either of these methods, or any later developed method to convert cellulose to hexane, may be carried out in the hydrodeoxygenation reactor 210. For example, in an aspect, hexane may be produced by the multi-step process as described in U.S. Pat. No. 5,516,960, which is incorporated by reference in its entirety. According to another embodiment, cellulose can be converted to hexane in the presence of hydrogen gas and a HZSM-5 zeolite catalyst at a temperature of about 210° C. According to yet another embodiment, cellulose may be converted to hexane in the presence of hydrogen and a binary Ir—ReOx/SiO$_2$+ZSM-5 catalyst system. According to still another embodiment, cellulose may be converted to hexane in the presence of hydrogen and a tungstosilicic acid and a modified Ru/C catalyst system. According to yet another embodiment, cellulose may be converted to hexane in the presence of hydrogen and a LiTaMoO$_6$ and Ru/C catalyst system in an aqueous phosphoric acid medium. Methods for converting cellulose to hexane in the presence of hydrogen can be further understood by reference to the Op de Beeck, et al., Energy & Environmental Science reference and/or the Liu, et al., ASC Sustainable Chem. Eng. References cited previously and incorporated herein by reference.

Referring again to FIG. 1, the bio-derived feedstock stream 127 comprising hexanes may be sent to a purification process (not shown) to separate the paraffinic, naphthenic, and/or olefinic hydrocarbons from the raw hydrodeoxygenation reactor product before the bio-derived feedstock stream 127 is fed to the aromatization reactor system 100, which is shown in FIG. 2. In some embodiments, this purification process may remove water, oxygenates, and heteroatoms or heavy hydrocarbons from the bio-derived feedstock stream 127. In some embodiments, unconverted glucose in the bio-derived feedstock stream 127 may be recycled to the biomass reactor system 200.

FIG. 2 presents a schematic diagram of an aspect of an aromatization reactor system 100 for producing aromatic hydrocarbons, in which a portion of the feedstock is a bio-derived feedstock that contains, for example, hexane produced from cellulose in a hydrodeoxygenation (HDO). As discussed with respect to the biomass reactor system illustrated in FIG. 1, the hydrogen produced from the aromatization reactor system 100 can be sent used in the biomass reactor system.

FIG. 2 illustrates an exemplary aromatization reactor system 100 for the production of aromatic hydrocarbons from naphtha feedstock 101. As shown in FIG. 2, the aromatization reactor system 100 comprises four catalytic aromatization reactors in series, designated as reactors 10, 20, 30, and 40. However, the aromatization reactor system 100 may comprise any suitable number and configuration of aromatization reactors, for example one, two, three, five, six, or more reactors in series. FIG. 2 illustrates the naphtha feedstock 101 being combined with a raffinate stream 119 comprising raffinate, before it is fed, via combined stream 102 to a purification process. If desired, the process may be carried out without raffinate stream 119. The purification process 80 purifies the combined stream 102 to create a purified stream 103, the composition of which forms the basis for the type of aromatic hydrocarbons being produced.

The bio-derived feedstock stream 127, received from the biomass reactor system 200, can be introduced into the aromatization reactor system, for example, into the combined stream 102, as shown in FIG. 2, before the purification process. Alternatively, the bio-derived feedstock stream 127 can be introduced, for example, into the purified stream 103 (not shown). As FIG. 2 illustrates, dry hydrogen recycle 116 may also be added to the purified stream 103 to produce hydrogen rich purified feed 104. Alternatively, the dry hydrogen recycle 116 may also be added to the into the combined stream 102, before the purification process. Also shown in FIG. 2 an oxygenate and/or nitrogenate stream 105 may be optionally added to the hydrogen rich purified feed 104 to produce reactor feedstream 106. In an aspect, the naphtha feedstock 101, the combined stream 102, the purified stream 103, the hydrogen rich purified feed 104, the optional oxygenate and/or nitrogenate stream 105, and the dry hydrogen recycle 116 can be combined prior to the first furnace 11 in virtually any order. Moreover, the purification process 80 also can be moved to any desired location prior to the first furnace 11, as a function of which specific individual or combined streams require purification, and what the specific impurities are encountered.

According to one aspect, the hydrogen recycle 115 may optionally be dried, via dryer 60 to form a dried hydrogen recycle 116. In another aspect, the dried hydrogen recycle 116 or hydrogen recycle 115 may be fresh hydrogen added from any appropriate source. Generally, the addition of hydrogen to the purified stream 103 can slow or prevent catalyst deactivation. For example, when the hydrogen concentration is sufficient it can prevent fouling and/or deactivation of the catalyst and carbonaceous species will be less likely to form and cover the active sites of a catalyst (fouling) and thereby prevent contact with the reactants (deactivation).

The hydrogen rich purified feed 104 may be fed to reactor 10 via furnace 11 or may optionally be combined with oxygenate and/or nitrogenate stream 105 to produce reactor feedstream 106. An oxygenate, a nitrogenate, or mixtures thereof may be added into the aromatization system at various times, in various locations, and in various manners, as discussed herein. Oxygenate and/or nitrogenate addition causes a specific amount of water and/or ammonia to be present in one or more aromatization reactors during the aromatization process. The presence of a specific amount of water and/or ammonia in an aromatization reactor can activate or enhance performance of the aromatization catalyst.

As aromatization reactions are highly endothermic, large temperature drops occur across each reactor. Therefore, each reactor 10, 20, 30, and 40 in the series may comprise a corresponding furnace 11, 21, 31, and 41, respectively, for preheating components to a desired temperature or maintaining a desired reaction rate. Alternatively, one or more reactors may share a common furnace where practical. According to an aspect, the aromatization reactor system 100 (for example reactors 10, 20, 30, and 40; furnaces 11, 21, 31, and 41; hydrogen separation process 50; dryer 60; purification-extraction process 70; and purification process 80; valves; pumps; heat exchangers; and the like) may be coupled to a computer system that may communicate with one or more components of the aromatization reactor system 100 so as to set or adjust operating parameters.

Traditional aromatization reactions are commonly run in a series of adiabatic reactors. In these reactors, no heat enters the reactor save the heat carried by the input streams. As the reaction proceeds through each reactor, the process stream loses heat. At these lower temperatures, catalyst activity is decreased, selectivity is high, and stability is good. At high temperatures catalyst activity increases, deactivation increases and selectivity decreases. Therefore, temperature must be optimized in order to achieve the best catalytic performance. Optimal temperature ranges differ depending upon the catalyst and the aromatization process being carried out. The use of a diluent heat source allows more time to be spent reacting near the optimal temperature. As an alternative to an adiabatic reactor, aromatization reactions may be carried out in an isothermal reactor, reactors in which the temperature remains constant by addition of heat.

Reactor feedstream 106 may be pre-heated in a first furnace 11, which heats the hydrocarbons to a desired temperature, thereby producing first reactor feed 107. First reactor feed 107 may be fed into reactor 10, where the hydrocarbons are contacted with an aromatization catalyst under suitable reaction conditions (for example, temperature, pressure, hydrogen to hydrocarbon mole ratio, or space velocity) for aromatizing one or more components in the feed to increase the content of aromatic hydrocarbons.

First reactor effluent 108 comprises aromatic hydrocarbons, unreacted feed, and other hydrocarbon compounds or by-products. First reactor effluent 108 may be pre-heated in second furnace 21. Second furnace 21 reheats the hydrocarbons to a desired temperature thereby producing second reactor feed 109. Second reactor feed 109 may be then fed into reactor 20, where the hydrocarbons are contacted with an aromatization catalyst under suitable reaction conditions for aromatizing one or more components in the feed to increase the content of aromatic hydrocarbons. Second reactor effluent 110 comprising aromatic hydrocarbons, unreacted feed, and other hydrocarbon compounds or by-products is recovered from reactor 20.

Second reactor effluent 110 may be pre-heated in third furnace 31, which again reheats the hydrocarbons to a desired temperature, thereby producing third reactor feed 111. Third reactor feed 111 may be then fed into reactor 30, where the hydrocarbons are contacted with an aromatization catalyst under suitable reaction conditions for aromatizing one or more components in the feed to increase the content of aromatic hydrocarbons. Third reactor effluent 112 comprising aromatic hydrocarbons, unreacted feed, and other hydrocarbon compounds or by-products is recovered from reactor 30.

Third reactor effluent 112 may be pre-heated in fourth furnace 41, which again reheats the hydrocarbons to a desired temperature, thereby producing fourth reactor feed 113. Fourth reactor feed 113 may be then fed into reactor 40, where the hydrocarbons are contacted with an aromatization catalyst under suitable reaction conditions for aromatizing one or more components in the feed to increase the content of aromatic hydrocarbons. Fourth reactor effluent 114 comprising aromatic hydrocarbons, unreacted feed, and other hydrocarbon compounds or by-products is recovered from reactor 40.

According to the embodiment illustrated in FIG. 2, the fourth reactor effluent 114 can be directed into further downstream reactors for additional conversion, or it may be fed into hydrogen separation process 50. Methods to separate the hydrogen recycle 115 from the reformate 117 in the hydrogen separation process 50 are well known. According to one embodiment, the hydrogen recycle 115 is not recycled to purified stream 103 and is instead sent to the biomass reactor system 200 as seen in FIG. 1. According to another embodiment as shown in FIG. 2, the hydrogen stream is split into hydrogen recycle 115 and hydrogen feed stream 125 going to biomass reactor system 200.

Reformate 117 may comprise aromatization reaction products from reactors 10, 20, 30, and 40 (including, aromatic hydrocarbons and non-aromatic hydrocarbons) in addition to any unreacted feed and other hydrocarbon compounds or by-products.

Oxygenates, nitrogenates, or mixtures thereof described herein may be used alone, in combination, or further combined to produce other suitable oxygenates or nitrogenates. In some embodiments, the oxygenate and/or nitrogenate may be contained within the same bifunctional compound. The oxygenate and/or nitrogenate may be added in any suitable physical phase such as a gas, liquid, or combinations thereof.

The oxygenate and/or nitrogenate may be added to one or more process streams and/or components via any suitable means for their addition, for example a pump, injector, sparger, bubbler, or the like. The oxygenate and/or nitrogenate may be introduced as a blend with a carrier. In some embodiments, the carrier can be hydrogen, a hydrocarbon, nitrogen, an inert gas, or mixtures thereof. In a preferred embodiment, the carrier is hydrogen.

The oxygenate and/or nitrogenate may be added at various locations within the aromatization system described herein. For example, the oxygenate and/or nitrogenate may be added to one or more process streams in the aromatization reactor system 100 as illustrated in FIG. 2, to one or more equipment components or vessels of the aromatization reactor system 100, or combinations thereof. In an embodiment, the oxygenate and/or nitrogenate may be added at one or more locations within a reaction zone defined by the aromatization system 100, wherein the reaction zone comprises process flow lines, equipment, and vessels wherein reactants are undergoing an aromatization reaction.

In one embodiment, the oxygenate and/or nitrogenate is added between the purification process 80 and the first furnace 11, either before the addition of the dry hydrogen recycle 116, or after the addition of the dry hydrogen recycle 116 as depicted in FIG. 2. Alternatively, the oxygenate and/or nitrogenate may be added within the purification process 80. However, it is also contemplated that the oxygenate and/or nitrogenate can be added at various other locations within the aromatization reactor system 100. For example, the oxygenate and/or nitrogenate can be added to the naphtha feedstock 101, the combined feed 102, the first reactor feed 107, the first reactor effluent 108, the second reactor feed 109, the second reactor effluent 110, the third reactor feed 111, the third reactor effluent 112, the fourth reactor feed 113, or combinations thereof. In addition, the oxygenate and/or nitrogenate could be added to the fourth reactor effluent 114, the hydrogen recycle 115, the dry hydrogen recycle 116, the reformate 117, the raffinate stream 119, or combinations thereof.

Furthermore, the oxygenate and/or nitrogenate can be added to any combination of the aforementioned streams, directly to any of the reactors 10, 20, 30, or 40, directly to the furnaces 11, 21, 31, 41, or combinations thereof. Likewise, the oxygenate and/or nitrogenate can be added directly to any other process equipment or component of the aromatization reactor system 100 such as a pump, value, port, tee, manifold, and the like. Finally, it is possible to add the oxygenate and/or nitrogenate to any process equipment or component upstream of the aromatization reactor system 100 such as a tank, pump, value, port, tee, manifold, and the like that supplies the naphtha feedstock 101 to the aromatization reactor system 100.

The addition of oxygenates and/or nitrogenates to a reforming process is described in detail in U.S. Pat. No. 7,932,425, which is incorporated herein by reference in its entirety. All manner of addition described therein may be used in the aromatization processes as described herein.

In embodiments, the effluent from the final aromatization reactor may comprise at least about 40 wt. % of the primary aromatic hydrocarbons by total weight of the effluent. In other embodiments, the effluent from the aromatization process may comprise from about 40 wt. % to about 80 wt. % of the primary aromatic hydrocarbon by total weight of the effluent. In some embodiments, the aromatization process may achieve from about 60 wt. % to about 100 wt. % conversion, alternatively from about 70 wt. % to about 90 wt. % conversion, with at least about 80 mol. % selectivity. In some embodiments, the primary aromatic hydrocarbons can comprise toluene, benzene, xylenes, and the like.

Referring again to FIG. 2, hydrogen recycle 115 may optionally be dried in dryer 60, thereby forming dry hydrogen recycle 116, which may be recycled into purified stream 103.

Reformate 117 is fed to purification-extraction process 70, which separates aromatics from non-aromatics to produce a raffinate stream 119 (comprised of non-aromatic hydrocarbons) and reactor by-products (not shown); and an aromatic hydrocarbon stream 118. In the embodiment illustrated in FIG. 2, raffinate stream 119 may be recycled into the combined stream 102 or may be sold as blend-stock for fuels. The aromatic hydrocarbon 118 may be sold, separated by fractionation into benzene toluene and/or xylenes, or otherwise used as desired. For the sake of simplicity, FIG. 2 does not illustrate the by-product streams that can be removed from aromatization reactor system 100 at various points throughout the system. However, persons of ordinary skill in the art are aware of the composition and location of such by-product streams. In some embodiments, raffinate stream 119 may be produced as a product.

Hydrogen separation processes 50 and purification-extraction processes 70 are well known in the art and are described in numerous patents, for example, U.S. Pat. No. 5,401,386 to Morrison et al. entitled "Reforming Process for Producing High-Purity Benzene," U.S. Pat. No. 5,877,367 to Witte entitled "Dehydrocyclization Process with Downstream Dimethylbenzene Removal", and U.S. Pat. No. 6,004,452 to Ash et al. entitled "Process for Converting Hydrocarbon Feed to High Purity Benzene and High Purity Paraxylene," each of which is incorporated herein by reference in its entirety. Generally, the extraction is either a liquid/liquid extraction or an extractive distillation. According to one embodiment, extractive distillation involves extractive distillation with N-substituted morpholines as the extractive distillation solvent. According to another embodiment, the extraction unit comprises an extractive distillation unit using an N-formylmorpholine solvent. Such a unit generally comprises an extractive distillation column and a stripper column. The extractive distillation column contacts the light fraction with the N-formylmorpholine solvent, suppressing the boiling point of the aromatic hydrocarbons and allowing the non-aromatic hydrocarbons to be taken overhead. The stripper column separates the remaining aromatic hydrocarbons from the N-formylmorpholine solvent using simple distillation. The non-aromatic hydrocarbon raffinate recovered from the extraction process may be sold for blending into fuel for automobiles, or recycled and added to the feed, which may increase overall yield of the process.

The aromatic hydrocarbon stream 118 shown in FIG. 2 can comprise, for example, up to about 60 wt. % bio-derived aromatic hydrocarbons produced from the bio-derived feedstock stream 127 generated from the biomass feedstream 201. As used herein "bio-derived aromatic hydrocarbons" refers to the portion of the aromatic hydrocarbons produced from the bio-derived feedstock. The aromatic hydrocarbon stream 118 can include at least about 10 wt. % bio-derived aromatic hydrocarbon, for example at least about 15 wt. % bio-derived aromatic hydrocarbon, for example, at least about 20 wt. % bio-derived aromatic hydrocarbon, for example at least about 25 wt. % bio-derived aromatic hydrocarbon, for example, at least about 30 wt. % bio-derived aromatic hydrocarbon, for example at least about 40 wt. % bio-derived aromatic hydrocarbon, for example, at least about 50 wt. % bio-derived aromatic hydrocarbon. Alternatively, the aromatic hydrocarbon stream 118 can include from about 5 wt. % to about 100 wt. % bio-derived aromatic hydrocarbon, from about 10 wt. % to about 90 wt. % bio-derived aromatic hydrocarbon, for example from about 20 wt. % to about 70 wt. % bio-derived aromatic hydrocarbon, for example from about 30 wt. % to about 60 wt. % bio-derived aromatic hydrocarbon, for example from about 40 wt. % to about 50 wt. % bio-derived aromatic hydrocarbon. Even if a portion of the resulting aromatic hydrocarbon is bio-derived aromatic hydrocarbon, much of the consumer perception problem of the polymers and products made from the aromatic hydrocarbons can be addressed.

Benzene, including up to 100 wt. % bio-derived benzene, can be used to make downstream products including, for example, styrene, cyclohexane, cumene, nitrobenzene, and the like. Styrene is generally produced by the alkylation of benzene with ethylene to produce ethylbenzene followed by catalytic dehydrogenation of ethylbenzene to styrene. Styrene is the monomer for polystyrene and various styrenic copolymers, and renewable styrene products that may be produced with the renewable benzene as described herein include polymers with diverse end uses that including polystyrene, ABS, styrene-butadiene rubber, and the like. Therefore, renewable styrene products that may be produced with the renewable benzene according to this disclosure can also be used to produce a wide variety of polymers with diverse end uses that include packaging, automotive applications, electronic parts, rubber articles, paper, housewares, tires, luggage, construction materials, carpeting, and toys.

Cyclohexane may be used as a solvent, in commercial or residential cleaning solutions, for the industrial production of adipic acid and caprolactam, nylon, and the like. Cumene may be used to thin paints, lacquers and enamels, may be a component of high octane fuels, and may also be used in the manufacture of phenol, acetone, acetophenone, and methylstyrene. Nitrobenzene may be used to produce lubricating oils, manufacture dyes, drugs, pesticides, synthetic rubber, aniline, and polyurethane. Other aromatics such as xylenes and toluene may be used as a solvent, to thin paints and varnishes, a cleaning agent, or as chemical precursors. For example, xylene is used to produce terephthalic acid which is a monomer for polyesters, particularly polyethylene terephthalate (PET).

Renewable styrene, cyclohexane, cumene, and nitrobenzene as disclosed herein can be used to produce any product that has heretofore been produced from styrene, cyclohexane, cumene, and nitrobenzene or styrene, cyclohexane, cumene, and nitrobenzene derivatives. Styrene, cyclohexane, cumene, and nitrobenzene which have been produced almost exclusively from petroleum products can now be produced in substantial part using renewable resources. Described herein are styrene, cyclohexane, cumene, and nitrobenzene products which are made from benzene having at least about 10 wt. % bio-derived benzene.

The aromatization catalyst may comprise an inorganic support, a Group 8-10 metal such as platinum, and one or more halides such as fluorine, chlorine, iodine, bromine, or combinations thereof. In some embodiments, the catalyst may comprise Group 8-10 metals on an inorganic support such as platinum on alumina, Pt/Re on alumina, or incorporate a Group 14 metal such as Pt/Sn on alumina and. In other embodiments, the catalyst may comprise Group 10, or platinum group, metals on a zeolitic support. Examples include Pt, Pt/Sn and Pt/Re on zeolitic supports which may comprise a binder and zeolites such as L-zeolites, ZSM-5, silicalite and beta; and Group 8-10 metals on alkali- and alkaline-earth exchanged L-zeolites. The catalyst may comprise an inorganic support further comprising a large-pore zeolite, charged with at least one Group 8-10 metal. In embodiments, the Group 8-10 metal may comprise platinum, which may be more selective for dehydrocyclization and which may be more stable under reforming reaction conditions than other Group 8-10 metals. In other embodiments, the catalyst may comprise a Group 7 metal such as rhenium, a group 11 metal such as gold, or a Group 14 metal or metalloid such as tin or germanium.

In one embodiment, the catalyst may comprise a non-acidic catalyst which may comprise a non-acidic zeolite support as the inorganic support, a Group 8-10 metal or other suitable metals, and one or more halides. Suitable halides include chloride, fluoride, bromide, iodide, or combinations thereof. Suitable Group 8-10 metals include iron, cobalt, nickel, ruthenium, rhodium, palladium, osmium, iridium, platinum, or combinations thereof.

Inorganic supports for aromatization catalysts (also termed reforming catalysts) can generally include any inorganic oxide. These inorganic supports include bound large pore aluminosilicates (zeolites), amorphous inorganic oxides and mixtures thereof. Large pore aluminosilicates include, but are not limited to, L-zeolite, Y-zeolite, mordenite, omega zeolite, beta zeolite and the like. Amorphous inorganic oxides include, but are not limited to, aluminum oxide, silicon oxide and titania. Suitable binding agents for the inorganic supports include, but are not limited to, silica, alumina, clays, titania, magnesium oxide, and combinations thereof.

The inorganic support may be a bound aluminosilicate, for example a bound zeolite. In embodiments, the aromatization catalyst may prepared on a bound zeolitic catalyst support, also described as a zeolitic catalyst support. Zeolite materials, both natural and synthetic, can have appropriate catalytic properties for many hydrocarbon processes, including aromatization. Thus, zeolites can include the group of natural or synthetic hydrated aluminosilicate minerals that typically contain alkali and alkaline metals. Zeolites are characterized by a framework structure that encloses interconnected cavities occupied by ion-exchangeable large metal cations such as potassium and water molecules permitting reversible dehydration. The actual formula of the zeolite may vary without changing the crystalline structure. In an embodiment, the mole ratio of silicon to aluminum (Si/Al) in the zeolite may vary from about 1.0 to about 3.5.

In embodiments, the aromatization catalyst support may comprise a large pore zeolite. The term "large-pore zeolite" may be defined as a zeolite having an effective pore diameter of from about 6 Angstroms (Å) to about 15 Å; alternatively, from about 7 Å to about 9 Å. Examples of large pore crystalline zeolites are type L-zeolite, zeolite X, zeolite Y, omega zeolite, beta zeolite, ZSM-4, ZSM-5, ZSM-10, ZSM-12, ZSM-20, REY, USY, RE-USY, LZ-210, LZ-210-A, LZ-210-M, LZ-210-T, SSZ-24, SSZ-26, SSZ-31, SSZ-33, SSZ-35, SSZ-37, SSZ-41, SSZ-42, SSZ-44, MCM-58, mordenite, mazzite, faujasite, and combinations thereof. In one embodiment, the large pore zeolite may comprise an isotypic framework structure. In one embodiment, the aromatization catalyst support may comprise L-zeolite.

L-Zeolite, its x-ray diffraction pattern, its properties, and methods for its preparation are described in detail in, U.S. Pat. No. 3,216,789, the content of which is hereby incorporated by reference. Zeolite X is described in U.S. Pat. No. 2,882,244. Mazzite is described in U.S. Pat. Nos. 4,503,023 and 4,021,447. Mordenite is described in U.S. Pat. No. 4,503,023. Zeolite Y is described in U.S. Pat. No. 3,130,007. U.S. Pat. Nos. 3,216,789; 2,882,244; 4,503,023; 4,021,447; and 3,130,007, are hereby incorporated herein by reference to show zeolites useful for aromatization processes.

In embodiments, the aromatization catalyst support may comprise a large pore L-zeolite. L-type zeolite catalyst supports are a sub-group of zeolitic catalyst supports. Typical L-type zeolites contain mole ratios of oxides in accordance with the following formula:

$$M_{2/n}O \cdot Al_2O_3 \cdot xSiO_2 \cdot yH_2O,$$

wherein "M" designates at least one exchangeable cation such as barium, calcium, cerium, lithium, magnesium, potassium, sodium, strontium, and zinc as well as non-metallic cations like hydronium and ammonium ions which may be replaced by other exchangeable cations without causing a substantial alteration of the basic crystal structure of the L-type zeolite. The "n" in the formula represents the valence of "M", "x" may be 2 or greater; and "y" is the number of water molecules contained in the channels or interconnected voids with the zeolite.

Bound potassium L-type zeolites, or KL zeolites, have been found to be particularly desirable. The term KL zeolite as used herein refers to L-type zeolites in which the principal cation M incorporated in the zeolite may comprise potassium. A KL zeolite may be cation-exchanged or impregnated with another metal and one or more halides to produce a platinum-impregnated, halided zeolite or a KL supported Pt-halide zeolite catalyst. In one embodiment, the zeolite may comprise type L zeolite. In embodiments, the aromatization catalyst may comprise a potassium L-type zeolite, hereafter referred to as KL-zeolite, which refers to L-type zeolites wherein the principal exchangeable cation M incorporated in the zeolite is potassium.

One or more Group 8-10 metals or other suitable metals such as rhenium can be added to the catalyst support to form a metallized catalyst support. The metal may be added to the catalyst support by employing a variety of known and conventional techniques, for example, ion-exchange, incipient wetness, pore fill, impregnation, vapor deposition, and the like. In embodiments, the platinum and optionally one or more halides may be added to the zeolite support by any suitable method, for example via impregnation with a solution of a platinum-containing compound and one or more halide-containing compounds. In one embodiment, the metal may be added to the catalyst support by impregnation with a metal-containing solution. The metal in the metal containing solution may comprise at least one metal from Group 8-10; alternatively, ruthenium, osmium, rhodium, iridium, palladium or platinum, or combinations thereof. In one embodiment, the metal may comprise platinum that may be added to the catalyst support via contact with a metal-containing solution containing at least one platinum-containing compound. Examples of suitable platinum-containing compounds for contact with the catalyst support include without limitation platinum compounds that form positively charged platinum complex ions in solution such as for example platinum salts such as chlorides and nitrates; platinum complexes with amines; or combinations thereof. For example, the platinum-containing compound can be any decomposable platinum-containing compound including, but not limited to, ammonium tetrachloroplatinate, chloroplatinic acid, diammineplatinum (II) nitrite, bis(ethylenediamine)platinum (II) chloride, platinum (II) acetylacetonate, dichlorodiammine platinum, platinum (II) chloride, tetraammineplatinum (II) hydroxide, tetraammineplatinum chloride, and tetraammineplatinum (II) nitrate. In one embodiment, the platinum source may comprise tetraamine platinum chloride (TAPC). The amount of platinum in the metallized catalyst support may range from about 0.1 wt. to about 5 wt. %; for example, from about 0.1 wt. to about 3 wt. %; for example, from about 0.3 wt. to about 1.8 wt. %.

In an aspect, the catalyst may comprise a large pore zeolite support with a platinum-containing compound and at least one halide. One or more halides may be added to the catalyst support by contact with a halide-containing compound to form a halided catalyst support. The halides may be added into the catalyst support separately; alternatively, the halides may be added to the catalyst support at the same time. Such halides may be incorporated during addition of a metal, alternatively, the halides may be incorporated in a separate step that may be pre- or post-addition of the metal, to form a halided, metallized catalyst support. Examples of suitable halides include without limitation fluoride, chloride, bromide, iodide, or combinations thereof. Such halides may be introduced, for example, as the ammonium halide compound.

In one embodiment, the catalyst may comprise a large pore zeolite support with a platinum-containing compound and at least one ammonium halide compound. The ammonium halide compound may comprise one or more compounds represented by the formula [NR$_4$]X, where X may comprise a halide and where R represents a hydrogen or a substituted or unsubstituted carbon chain molecule having about 1 to about 20 carbons wherein each R may be the same or different. In one embodiment, R may comprise methyl, ethyl, propyl, butyl, or combinations thereof. Examples of a suitable organic ammonium compound represented by the formula [NR$_4$]X may include ammonium chloride, ammonium fluoride, and tetraalkylammonium halides such as tetramethylammonium chloride (TMAC), tetramethylammonium fluoride (TMAF), tetraethylammonium chloride, tetraethylammonium fluoride, tetrapropylammonium chloride, tetrapropylammonium fluoride, tetrabutylammonium chloride, tetrabutylammonium fluoride, methyltriethylammonium chloride, methyltriethylammonium fluoride, or combinations thereof.

In one aspect, the aromatization catalyst may comprise a metallized, halided support and the amount of halide in the catalyst ranges from about 0.05 wt. % to about 5.0 wt. %. In one embodiment, the halided catalyst support may comprise chloride present in an amount of from about 0.1 wt. % to about 5 wt. %; for example, from about 0.1 wt. % to about 4 wt. %; for example, from about 0.3 wt. % to about 3.0 wt. %. In one embodiment, the halided catalyst support may comprise fluoride present in one amount of from about 0.1 wt. % to about 5 wt. %; for example, from about 0.1 wt. % to about 3 wt. %; for example, from about 0.3 wt. % to about 1.8 wt. %. In one embodiment, the halided catalyst support may comprise both chloride and fluoride, which may be present in a Cl:F ratio of from about 1:10 to about 10:1; for example, from about 1:5 to about 5:1; for example, from about 1:2 to about 2:1.

Examples of suitable aromatization catalysts are also disclosed in U.S. Pat. No. 7,153,801 to Wu entitled "Aromatization Catalyst and Methods of Making and Using Same," and U.S. Pat. No. 6,812,180 to Fukunaga entitled "Method for Preparing Catalyst," each of which is incorporated herein by reference in their entirety.

The processes as described can be carried out with any art recognized selective catalysts. In one embodiment, the catalyst for use in the described process may comprise a low-acidity silica-bound potassium L-type zeolite support, platinum, chloride, and fluoride. In this embodiment, the aromatization catalyst selectively converts near-linear $C_6$ hydrocarbons (for example, $C_6$ hydrocarbons with no more than one branch), but may not readily convert $C_6$ hydrocarbons having more than one branch, for example, 2,2-dimethylbutane. This selective catalyst readily converted near-linear $C_6$ hydrocarbons to aromatic hydrocarbons at greater than about 75 mol. % aromatics selectivity; for example, greater than about 80 mol. % aromatics selectivity; for example, greater than about 83 mol. % aromatics selectivity.

Catalysts for use in the process as described generally see a decline in catalytic activity that occurs as the catalyst is used under commercial reaction conditions. A catalyst is generally considered spent when it has reached an unacceptable level in one or more of, activity, conversion, selectivity, yield or other operating parameter. Regenerable catalysts are appropriate for use in the processes as described, and the catalysts can be subjected to any art recognized regeneration chemistry. For example, transition metal catalysts are often regenerated by contacting the spent catalyst with a halogen-containing stream, for example, chlorine or fluorine and then decoking the catalyst in an oxygen stream.

The aromatization reactions may occur under process conditions that thermodynamically favor the dehydrocyclization (aromatization) reaction and limit the undesirable hydrocracking reactions. Operating ranges for a typical aromatization process, such as an aromatization process as disclosed herein, may include reactor inlet temperatures between about 370° C. and about 570° C., for example between about 430° C. and about 550° C.; a system pressure between about 0 pounds per square inch gauge (psig) (0 KPa) and about 580 psig (3999 KPa), for example from about 0 psig (0 KPa) to about 365 psig (2517 KPa); a hydrogen rate sufficient to yield a hydrogen to hydrocarbon mole ratio for the feed to the reforming reactor zone between about 0.1 and about 20, for example from about 3 to about 10, for example from about 1.5 to about 6; and, a liquid hourly space velocity for the hydrocarbon feed over the aromatization catalyst of between about 0.1 and about 10.

Examples of aromatization catalysts and aromatization reactor systems suitable for use with the methods described herein are the AROMAX® Process and catalyst technologies available from the Chevron Phillips Chemical Company of The Woodlands, Tex., USA. A specific example of a suitable commercially available aromatization catalyst is the AROMAX® II Catalyst available from Chevron Phillips Chemical Company LP of The Woodlands, Tex., USA.

EXAMPLES

Figure 3:
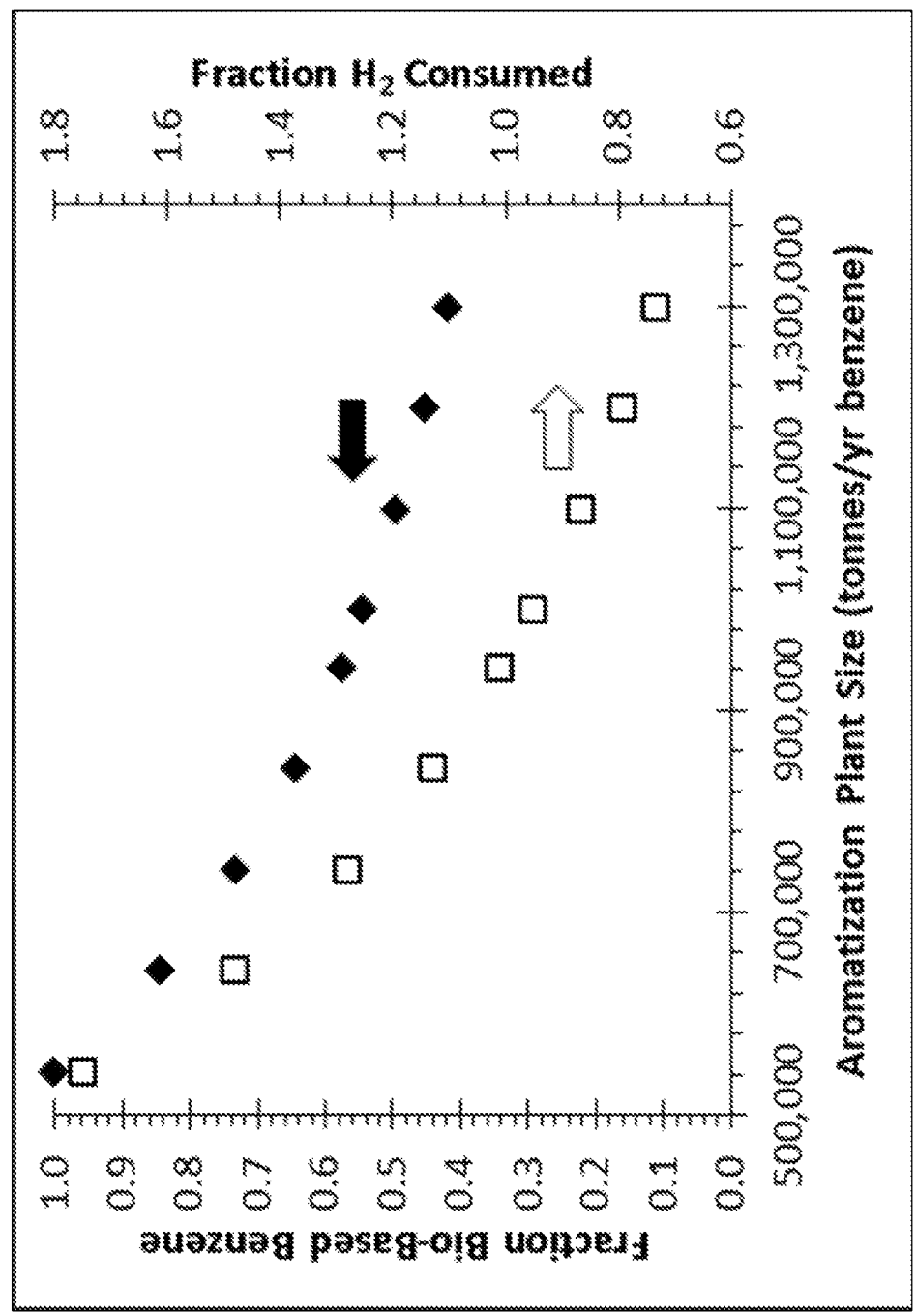
FIG. 3 illustrates the fraction of bio-derived benzene produced by an aromatization plant, and the overall fraction of hydrogen produced by the aromatization plant that is consumed by the biomass reactor system, for aromatization plants of different sizes, assuming a world-scale biomass hydrodeoxygenation reactor that consumes about 1.25 million tonnes/year of glucose is providing the bio-derived feedstock and $H_2$.

Several prophetic examples are provided below, and are also illustrated by FIG. 3, which shows the fraction of bio-derived benzene produced by an aromatization plant, and the overall fraction of hydrogen produced by the aromatization plant that is consumed by the biomass reactor system, for aromatization plants of different sizes. This plot assumes a world scale biomass hydrodeoxygenation reactor that consumes about 1.25 million tonnes/year of glucose for the production of hexane. This hexane is then converted to benzene in the aromatization reactor. For the illustration, perfect selectivity from glucose to benzene is assumed. The white (open) squares on this plot represent the fraction of $H_2$ consumed, and the black (filled) diamonds represent the fraction of bio-derived benzene produced.

Prophetic Example 1

A biomass reactor is fed 1.25 million tonnes of glucose per year (143 tonnes per hour) producing 600,000 tonnes per year of hexane (68 tonnes per hour) and consuming 98,000 tonnes per year (11 tonnes per hour) of hydrogen, based on a 100 mol. % yield (mol/mol) of hexane from glucose, as illustrated in Equation 9. The biomass reactor is located proximate to a typical aromatization facility which produces on the order of 1 million tonnes per year (114 tonnes per hour) of benzene and 103,000 tonnes per year (12 tonnes per hour) of hydrogen. The rates on an hour basis assumed 8760 operating hours/yr. In this example, the aromatization facility will net about 5,000 tonnes per year (0.6 tonnes per hour) of hydrogen after supplying the 98,000 tonnes per year (11 tonnes/hour) of hydrogen to the biomass reactor.

Based on a theoretical 100 mol. % yield of benzene from bio-derived n-hexane, the benzene produced in this example would be approximately 54 wt. % bio-derived.

Prophetic Example 2

A biomass reactor is fed 1.25 million tonnes of glucose per year (143 tonnes per hour) producing 600,000 tonnes per year of hexane (68 tonnes per hour) and consuming 98,000 tonnes per year (11 tonnes per hour) of hydrogen. The biomass reactor is located proximate a typical aromatization facility which produces on the order of 744,000 tonnes per year (85 tonnes per hour) of benzene and 76,000 tonnes per year (9 tonnes per hour) of hydrogen. An additional ~21,000 tonnes/yr. of hydrogen (2.4 tonnes per hour) which is produced via SMR is also sent to the process. In this example, all hydrogen produced at the aromatization facility and the 21,000 tonnes/yr. from the SMR is consumed by the biomass reactor so that the overall net hydrogen availability is near zero.

Based on a theoretical 100 mol. % conversion of bio-derived n-hexane, the benzene produced in this example will comprise about 73 wt. % bio-derived benzene.

Prophetic Example 3

In a biomass hydrodeoxygenation (HDO) reactor, cellulose can be converted to n-hexane in the presence of hydrogen and a binary Ir—ReOx/$SiO_2$+ZSM-5 catalyst system, for example, as set out in Liu, et al., One-Pot Conversion of Cellulose into n-Hexane over the IR-ReO$_x$/$SiO_2$ Catalyst Combined with HZSM-5, ASC Sustainable Chem. Eng. 2014, 2, 1819-1827. Some or all of the hexane produced in this HDO fashion can be supplied as at least a portion of the feed to an aromatization reactor, and typically will be blended with naphtha in some ratio. Because the biomass reactor system and the aromatization reactor system are integrated, the hexane produced from cellulose in the HDO reactor, typically in combination with naphtha, can be converted to benzene in the aromatization reactor, and hydrogen produced in the aromatization reactor can be employed in the integrated process.

Although specific embodiments have been illustrated and described herein, it should be appreciated that any arrangement configured to achieve the same purpose may be substituted for the specific embodiments shown. This disclosure is intended to cover any and all adaptations or variations of various embodiments. Combinations of the above embodiments, and other embodiments not described herein, will be apparent to those of skill in the art upon reviewing the above description.

ASPECTS

The following enumerated aspects are provided as non-limiting examples:

1. A method for producing a bio-derived aromatic hydrocarbon, comprising:
   a) contacting a biomass with hydrogen in the presence of a hydrodeoxygenation catalyst in at least one hydrodeoxygenation reactor unit, under conditions that produce a bio-derived feedstock further comprising paraffinic, naphthenic, and olefinic hydrocarbons;
   b) introducing the bio-derived feedstock into at least one aromatization reactor unit and contacting the bio-derived feedstock with an aromatization catalyst under conditions that produce an aromatic hydrocarbon and hydrogen; and
   c) providing at least a portion of the hydrogen produced in the at least one aromatization reactor to the at least one hydrodeoxygenation reactor for contacting the biomass.
2. The method of aspect 1, wherein the hydrodeoxygenation reactor unit is located proximate to the at least one aromatization reactor unit.
3. The method of any of aspects 1-2, wherein the bio-derived feedstock comprises convertible hydrocarbons.
4. The method of any of aspects 1-3, wherein the bio-derived feedstock comprises convertible $C_6$-$C_8$ species.
5. The method of any one of aspects 1-4, wherein the bio-derived feedstock comprises $C_6$ to $C_8$ paraffinic, naphthenic, and olefinic hydrocarbons.
6. The method of any one of aspects 1-5, wherein the bio-derived feedstock comprises a hexane.
7. The method of any one of aspects 1-6, wherein the bio-derived feedstock comprises n-hexane, 2-methylpentane, 3-methylpentane, 2,2-dimethylbutane, or 2,3-dimethylbutane.
8. The method of any one of aspects 1-7, wherein the aromatic hydrocarbon comprises benzene, toluene, or xylenes.
9. The method of any one of aspects 1-8, wherein the aromatic hydrocarbon comprises benzene.
10. The method of any one of aspects 1-9, wherein the biomass comprises a cellulose, a sugar, a starch, a lignocellulose, a hemicellulose, a lignin, or combinations thereof.
11. The method of any one of aspects 1-10, wherein the biomass comprises cellulose.
12. The method of any one of the preceding aspects, wherein the hydrodeoxygenation reaction is carried out at a temperature of at least about 180° C.
13. The method of any one of the preceding aspects, wherein the hydrodeoxygenation reaction is carried out a pressure of from about 50 psig (345 KPa) to about 2000 psig (13790 KPa).
14. The method of any one of the preceding aspects, wherein the hydrodeoxygenation catalyst is selected from those having metal hydrogenation and/or acidic active sites.
15. The method of any one of the preceding aspects, wherein (a) the step of contacting the biomass with hydrogen in the presence of the hydrodeoxygenation catalyst further produces methane, and (b) wherein the method further comprises a step of contacting the methane with steam and a steam reforming catalyst under conditions that produce hydrogen.
16. The method of aspect 15, further comprising the step of providing at least a portion of the hydrogen produced in the steam reformer to the at least one hydrodeoxygenation reactor unit for contacting the biomass.
17. The method of any one of the preceding aspects, further comprising combining a naphtha feedstock with the bio-derived feedstock to form a combined stream and introducing the combined stream into the at least one aromatization reactor unit and contacting the combined stream with the aromatization catalyst under conditions that produce the aromatic hydrocarbon and hydrogen.
18. The method of aspect 17, further comprising heating the naphtha feedstock and the bio-derived feedstock prior to introduction to the at least one aromatization reactor unit.
19. The method of aspect 17, wherein the aromatic hydrocarbon is separated from the hydrogen prior to providing at least a portion of the hydrogen produced in the at least one aromatization reactor unit to the at least one hydrodeoxygenation reactor unit.
20. The method of aspects 17, wherein the aromatic hydrocarbon is separated from the hydrogen prior to providing at least a portion of the hydrogen produced in the at least one aromatization reactor unit to both the at least one hydrodeoxygenation reactor unit and the at least one aromatization reactor unit.
21. The method of any one of the preceding aspects, wherein the bio-derived feedstock comprises a hexane and the aromatic hydrocarbon comprises benzene.
22. The method of any one of the preceding aspects, wherein the aromatization catalyst comprises an inorganic support, a Group 8-10 metal, and one or more halides.
23. The method of aspect 25, wherein the Group 8-10 metal is platinum and the halides are selected from one or more of fluorine, chlorine, iodine, or bromine.
24. The method of aspect 25, wherein the inorganic support is selected from one or more of silica, alumina, clays, titania, magnesium oxide and combinations thereof.
25. The method of any one of aspects 1-22, wherein the aromatization catalyst comprises an inorganic support, a metal selected from platinum, Pt/Sn or Pt/Re, and one or more halides.
26. The method of aspect 22 wherein the inorganic support is a zeolitic support further comprised of a zeolite and a binder; the binder selected from one or more of silica, or alumina and combinations thereof.
27. The method of aspect 26, wherein the zeolite is selected from L-zeolite, zeolite X, zeolite Y, omega zeolite, beta zeolite, ZSM-4, ZSM-5, ZSM-10, ZSM-12, ZSM-20, REY, USY, RE-USY, LZ-210, LZ-210-A, LZ-210-M, LZ-210-T, SSZ-24, SSZ-26, SSZ-31, SSZ-33, SSZ-35, SSZ-37, SSZ-41, SSZ-42, SSZ-44, MCM-58, mordenite, mazzite, faujasite, or combinations thereof.
28. The method of aspect 17, wherein the naphtha feedstock is purified prior to or after combining with the bio-derived feedstock to remove one or more of nitrogen, oxygen and/or sulfur.
29. The method of aspect 28, wherein the bio-derived feedstock comprises hexane and the naphtha feedstock is combined with the hexane after purification.

30. The method of any of aspects 1-29, wherein all of the hydrogen required to produce the bio-derived feedstock in the at least one hydrodeoxygenation reactor unit is provided from the at least one aromatization reactor unit.
31. The method of any of aspects 1-29, wherein at least about 5% of the hydrogen required to produce the bio-derived feedstock in the at least one hydrodeoxygenation reactor unit is provided from the at least one aromatization reactor unit.
32. The method of any of aspects 1-29, wherein at least about 10% of the hydrogen required to produce the bio-derived feedstock in the at least one hydrodeoxygenation reactor unit is provided from the at least one aromatization reactor unit.
33. The method of any of aspects 1-29, wherein at least about 20% of the hydrogen required to produce the bio-derived feedstock in the at least one hydrodeoxygenation reactor unit is provided from the at least one aromatization reactor unit.
34. The method of any of aspects 1-29, wherein at least about 30% of the hydrogen required to produce the bio-derived feedstock in the at least one hydrodeoxygenation reactor unit is provided from the at least one aromatization reactor unit.
35. The method of any of aspects 1-29, wherein at least about 40% of the hydrogen required to produce the bio-derived feedstock in the at least one hydrodeoxygenation reactor unit is provided from the at least one aromatization reactor unit.
36. The method of any of aspects 1-29, wherein at least about 50% of the hydrogen required to produce the bio-derived feedstock in the at least one hydrodeoxygenation reactor unit is provided from the at least one aromatization reactor unit.
37. The method of any of aspects 1-29, wherein at least about 60% of the hydrogen required to produce the bio-derived feedstock in the at least one hydrodeoxygenation reactor unit is provided from the at least one aromatization reactor unit.
38. The method of any of aspects 1-29, wherein at least about 70% of the hydrogen required to produce the bio-derived feedstock in the at least one hydrodeoxygenation reactor unit is provided from the at least one aromatization reactor unit.
39. The method of any of aspects 1-29, wherein at least about 80% of the hydrogen required to produce the bio-derived feedstock in the at least one hydrodeoxygenation reactor unit is provided from the at least one aromatization reactor unit.
40. The method of any of aspects 1-29, wherein at least about 90% of the hydrogen required to produce the bio-derived feedstock in the at least one hydrodeoxygenation reactor unit is provided from the at least one aromatization reactor unit.
41. The method of any of aspects 1-40, wherein the aromatic hydrocarbon is benzene, and at least about 10 percent of the benzene is made from the biomass.
42. The method of any of aspects 1-40, wherein the aromatic hydrocarbon is benzene, and at least about 20 percent of the benzene is made from the biomass.
43. The method of any of aspects 1-40, wherein the aromatic hydrocarbon is benzene, and at least about 30 percent of the benzene is made from the biomass.
44. The method of any of aspects 1-40, wherein the aromatic hydrocarbon is benzene, and at least about 40 percent of the benzene is made from the biomass.
45. The method of any of aspects 1-40, wherein the aromatic hydrocarbon is benzene, and at least about 50 percent of the benzene is made from the biomass.
46. The method of any of aspects 1-40, wherein the aromatic hydrocarbon is benzene, and at least about 60 percent of the benzene is made from the biomass.
47. The method of any of aspects 1-40, wherein the aromatic hydrocarbon is benzene, and at least about 70 percent of the benzene is made from the biomass.
48. The method of any of aspects 1-40, wherein the aromatic hydrocarbon is benzene, and at least about 80 percent of the benzene is made from the biomass.
49. The method of any of aspects 1-40, wherein the aromatic hydrocarbon is benzene, and at least about 90 percent of the benzene is made from the biomass.
50. The method of any of aspects 1-40, wherein the aromatic hydrocarbon is benzene, all of the benzene is made from the biomass.
51. The method of any of aspects 1-40, wherein the aromatic hydrocarbon is benzene, and from about 10 percent to about 40 percent of the benzene is made from the biomass.
52. A reactor system for producing aromatic hydrocarbons comprising:
a) a first feed pipe for supplying a first feed stream comprising naphtha;
b) a second feed pipe for supplying a second feed stream comprising a bio-derived feedstock comprising paraffinic, naphthenic, and olefinic hydrocarbons, in which the second feed pipe combines with the first feed pipe to form a reactant stream pipe;
c) a separation unit having an inlet and an outlet, situated in line with the first feed pipe, the second feed pipe, or the reactant stream pipe, configured to receive, respectively, the first feed stream, the second feed stream, or the reactant stream, and to discharge, respectively, a purified first feed stream, a purified second feed stream, or a purified reactant stream; and
d) an at least one aromatization reactor unit having an inlet to accept the reactant stream or the purified reactant stream, and further comprising an aromatization catalyst bed which converts at least a portion of the bio-derived feedstock to one or more aromatic hydrocarbons and hydrogen.
53. The method of aspect 52, wherein the bio-derived feedstock comprises convertible hydrocarbons.
54. The method of any of aspects 52-53, wherein the bio-derived feedstock comprises convertible $C_6$-$C_8$ species.
55. The method of any one of aspects 52-54, wherein the bio-derived feedstock comprises $C_6$ to $C_8$ paraffinic, naphthenic, and olefinic hydrocarbons.
56. The method of any one of aspects 52-55, wherein the bio-derived feedstock comprise a hexane.
57. The method of any one of aspects 52-56, wherein the bio-derived feedstock comprises n-hexane, 2-methylpentane, 3-methylpentane, 2,2-dimethylbutane, or 2,3-dimethylbutane.
58. The method of any one of aspects 52-57, wherein the aromatic hydrocarbon comprises benzene, toluene, or xylenes.
59. The method of any one of aspects 52-58, wherein the aromatic hydrocarbon comprises benzene.
60. The reactor system of any of aspects 52-59, further comprising a biomass reactor unit located proximate to the at least one aromatization reactor unit which supplies the second feed stream comprising the bio-derived feedstock to the second feed pipe.
61. The reactor system of aspect 60, wherein the hydrodeoxygenation reactor unit comprises an inlet configured to accept a starting material selected from cellulose, sugars, starch, lignocellulose, hemicellulose, lignin, or combinations thereof, and further comprises an outlet for discharging to the bio-derived feedstock to the second feed pipe.
62. The reactor system of any one of aspects 59-61, further comprising a separation system in fluid communication and downstream of the at least one aromatization reactor unit, which separates the one or more aromatic hydrocarbons from the hydrogen.
63. The reactor system of aspect 62, further comprising a pipe downstream of the separation system which supplies at least a portion of the hydrogen from the separation system to the hydrodeoxygenation reactor unit.
64. A reactor system for producing aromatic hydrocarbons from a renewable source, the system comprising:
a) at least one hydrodeoxygenation reactor unit comprising a first inlet for supplying a reactant stream comprising a biomass, a second inlet for supplying hydrogen, a hydrodeoxygenation catalyst bed, and an outlet for discharging a bio-derived feedstock into a first transfer pipe;
b) at least one aromatization reactor unit proximate to the at least one hydrodeoxygenation reactor, comprising an inlet for supplying a reactant stream comprising the bio-derived feedstock from the first transfer pipe and naphtha from a second transfer pipe, an aromatization catalyst bed, and an outlet for discharging a reactor effluent stream comprising one or more aromatic hydrocarbons and hydrogen;
c) a separation system for separating the reactor effluent into one or more aromatic hydrocarbons, hydrogen, and a raffinate; and
d) a third transfer pipe for supplying the hydrogen from the separation system to the second inlet of the hydrodeoxygenation reactor unit.
65. The method of aspect 64, wherein the bio-derived feedstock comprises convertible hydrocarbons.
66. The method of any of aspects 64-65, wherein the bio-derived feedstock comprises convertible $C_6$-$C_8$ species.
67. The method of any one of aspects 64-66, wherein the bio-derived feedstock comprises $C_6$ to $C_8$ paraffinic, naphthenic, and olefinic hydrocarbons.
68. The method of any one of aspects 64-67, wherein the bio-derived feedstock comprise a hexane.
69. The method of any one of aspects 64-68, wherein the bio-derived feedstock comprises n-hexane, 2-methylpentane, 3-methylpentane, 2,2-dimethylbutane, or 2,3-dimethylbutane.
70. The method of any one of aspects 64-69, wherein the aromatic hydrocarbon comprises benzene, toluene, or xylenes.
71. The method of any one of aspects 64-70, wherein the aromatic hydrocarbon comprises benzene.
72. The reactor system of any of aspects 64-71, wherein the bio-derived feedstock comprises hexane and the one or more aromatic hydrocarbons comprises benzene.
73. The reactor system of any one of aspects 64-72, wherein the at least one hydrodeoxygenation reactor unit comprises at least two reactors.
74. The reactor system of any one of aspects 64-73, wherein the at least one aromatization reactor unit comprises at least two reactors.
75. The reactor system of any one of aspects 64-74, wherein the hydrodeoxygenation catalyst bed comprises an acidic catalyst; a catalyst based on molybdenum, rhenium, iron, ruthenium, osmium, cobalt, rhodium, iridium, nickel, palladium, or platinum; an Ir—Re catalyst; or a ZSM-5 zeolite.
76. The reactor system of any one of aspects 64-75, wherein the aromatization catalyst comprises an inorganic support, a Group 8-10 metal, and one or more halides.
77. The reactor system of aspect 76, wherein the Group 8-10 metal is platinum and the halides are selected from one or more of fluorine, chlorine, iodine, or bromine.
78. The reactor system of aspect 77, wherein the inorganic support is selected from one or more of silica, alumina, a zeolite, clays, titania, magnesium oxide, or combinations thereof.
79. The reactor system of any one of aspects 76-78, wherein the aromatization catalyst comprises an inorganic support, a metal selected from platinum, Pt/Sn or Pt/Re, and one or more halides.
80. The reactor system of any one of aspects 76-79, wherein the inorganic support is alumina or a zeolite.
81. The reactor system of any one of aspects 78-80, wherein the zeolite is selected from L-zeolite, zeolite X, zeolite Y, omega zeolite, beta zeolite, ZSM-4, ZSM-5, ZSM-10, ZSM-12, ZSM-20, REY, USY, RE-USY, LZ-210, LZ-210-A, LZ-210-M, LZ-210-T, SSZ-24, SSZ-26, SSZ-31, SSZ-33, SSZ-35, SSZ-37, SSZ-41, SSZ-42, SSZ-44, MCM-58, mordenite, mazzite, faujasite, or combinations thereof.
82. The reactor system of any one of aspects 64-81, wherein the bio-derived feedstock comprises at least 95% hexane and the one or more aromatic hydrocarbons comprises at least 95% benzene.
83. The reactor system of any one of claims 64-81, wherein the bio-derived feedstock comprises at least 98 wt. % hexane and the one or more aromatic hydrocarbons comprises at least 98 wt. % benzene.
84. A method for producing renewable styrene comprising:
contacting benzene with ethylene under conditions to produce ethylbenzene, wherein the benzene comprises at least about 10 wt. % bio-derived benzene; and
dehydrogenating the ethylbenzene to produce a styrene product.
85. The method of aspect 84, wherein the benzene contains at least 15 wt. % bio-derived benzene.
86. The method of aspect 84, wherein the benzene contains at least 20 wt. % bio-derived benzene.
87. The method of aspect 84, wherein the benzene contains at least 30 wt. % bio-derived benzene.
88. The method of aspect 84, wherein the benzene contains at least 40 wt. % bio-derived benzene.
89. The method of aspect 84, wherein the benzene contains at least 50 wt. % bio-derived benzene.
90. The method of aspect 84, wherein the benzene contains at least 60 wt. % bio-derived benzene.
91. The method of aspect 84, wherein the benzene contains at least 70 wt. % bio-derived benzene.
92. The method of aspect 84, wherein the benzene contains at least 80 wt. % bio-derived benzene.
93. The method of aspect 84, wherein the benzene contains at least 90 wt. % bio-derived benzene.

94. The method of aspect 84, wherein the benzene contains 100 wt. % bio-derived benzene.
95. The method of aspect 84, wherein the benzene contains from about 15 wt. % to about 60 wt. % bio-derived benzene.
96. A method for producing renewable styrene comprising:
   a) contacting a biomass with hydrogen in the presence of a hydrodeoxygenation catalyst in at least one hydrodeoxygenation reactor unit, under conditions that produce bio-derived feedstocks comprising hexanes;
   b) introducing the bio-derived feedstocks in combination with a naphtha reactant stream into at least one aromatization reactor unit and contacting the bio-derived feedstocks and naphtha with an aromatization catalyst under conditions that produce benzene and hydrogen;
   c) providing at least a portion of the hydrogen produced in the at least one aromatization reactor unit to the at least one hydrodeoxygenation reactor unit for contacting the biomass;
   d) contacting the benzene with ethylene under conditions to produce ethylbenzene, wherein the benzene comprises at least about 10 wt. % bio-derived benzene; and
   e) dehydrogenating the ethylbenzene to produce a styrene product.
97. The method of aspect 96, wherein the bio-derived feedstocks comprise convertible hydrocarbons.
98. The method of any of aspects 96-97, wherein the bio-derived feedstocks comprise convertible $C_6$-$C_8$ species.
99. The method of any one of aspects 96-98, wherein the bio-derived feedstocks comprise $C_6$ to $C_8$ paraffinic, naphthenic, and olefinic hydrocarbons.
100. The method of any one of aspects 96-99, wherein the bio-derived feedstocks comprise a hexane.
101. The method of any one of aspects 96-100, wherein the bio-derived feedstocks comprise n-hexane, 2-methylpentane, 3-methylpentane, 2,2-dimethylbutane, or 2,3-dimethylbutane.
102. The method of any of aspects 96-101, wherein the benzene contains at least 15 wt. % bio-derived benzene.
103. The method of any of aspects 96-101, wherein the benzene contains at least 20 wt. % bio-derived benzene.
104. The method of any of aspects 96-101, wherein the benzene contains at least 30 wt. % bio-derived benzene.
105. The method of any of aspects 96-101, wherein the benzene contains at least 40 wt. % bio-derived benzene.
106. The method of any of aspects 96-101, wherein the benzene contains at least 50 wt. % bio-derived benzene.
107. The method of any of aspects 96-101, wherein the benzene contains at least 60 wt. % bio-derived benzene.
108. The method of any of aspects 96-101, wherein the benzene contains at least 70 wt. % bio-derived benzene.
109. The method of any of aspects 96-101, wherein the benzene contains at least 80 wt. % bio-derived benzene.
110. The method of any of aspects 96-101, wherein the benzene contains at least 90 wt. % bio-derived benzene.
111. The method of any of aspects 96-101, wherein the benzene contains 100 wt. % bio-derived benzene.
112. The method of aspect 96, wherein the benzene contains from about 15 wt. % to about 60 wt. % bio-derived benzene.

I claim:

1. A method for producing a bio-derived aromatic hydrocarbon, comprising:
   a) contacting a biomass with hydrogen in the presence of a hydrodeoxygenation catalyst in at least one hydrodeoxygenation reactor unit, under conditions that produce a bio-derived feedstock further comprising paraffinic, naphthenic, and/or olefinic hydrocarbons;
   b) introducing the bio-derived feedstock into at least one aromatization reactor unit and contacting the bio-derived feedstock with an aromatization catalyst under conditions that produce an aromatic hydrocarbon and hydrogen; and
   c) providing at least a portion of the hydrogen produced in the at least one aromatization reactor to the at least one hydrodeoxygenation reactor for contacting the biomass,
   wherein the biomass comprises a cellulose, a sugar, a starch, a lignocellulose, a hemicellulose, a lignin, or combinations thereof.

2. The method of claim 1, wherein the hydrodeoxygenation reactor unit is located proximate to the at least one aromatization reactor unit.
3. The method of claim 1, wherein the bio-derived feedstock comprises C6 to C8 paraffinic, naphthenic, and olefinic hydrocarbons.
4. The method of claim 1, wherein the bio-derived feedstock comprises a hexane.
5. The method of claim 1, wherein the aromatic hydrocarbon comprises one or more of benzene, toluene, or xylenes.
6. The method of claim 1, wherein the hydrodeoxygenation reaction is carried out at a temperature of at least about 180° C. and at a pressure of from about 50 psig (345 KPa) to about 2000 psig (13790 KPa).
7. The method of claim 1, wherein (a) the step of contacting the biomass with hydrogen in the presence of the hydrodeoxygenation catalyst further produces methane, (b) the method further comprises a step of contacting the methane with steam and a steam reforming catalyst under conditions that produce hydrogen, and (c) the method further comprises a step of providing at least a portion of the hydrogen produced in the steam reformer to the at least one hydrodeoxygenation reactor unit for contacting the biomass.
8. The method of claim 1, further comprising combining a naphtha feedstock with the bio-derived feedstock to form a combined stream and introducing the combined stream into the at least one aromatization reactor unit and contacting the combined stream with the aromatization catalyst under conditions that produce the aromatic hydrocarbon and hydrogen.
9. The method of claim 8, wherein the aromatic hydrocarbon is separated from the hydrogen prior to providing at least a portion of the hydrogen produced in the at least one aromatization reactor unit to both the at least one hydrodeoxygenation reactor unit and the at least one aromatization reactor unit.
10. The method of claim 1, wherein the aromatization catalyst comprises an inorganic support, a Group 8-10 metal, and one or more halides.
11. The method of claim 10, wherein the inorganic support is a zeolitic support further comprised of a zeolite and a binder; the binder selected from one or more of silica, or alumina and combinations thereof.
12. The method of claim 11, wherein the zeolite is selected from L-zeolite, zeolite X, zeolite Y, omega zeolite, beta zeolite, ZSM-4, ZSM-5, ZSM-10, ZSM-12, ZSM-20, REY, USY, RE-USY, LZ-210, LZ-210-A, LZ-210-M, LZ-210-T, SSZ-24, SSZ-26, SSZ-31, SSZ-33, SSZ-35, SSZ-37, SSZ-41, SSZ-42, SSZ-44, MCM-58, mordenite, mazzite, faujasite, or combinations thereof.

13. The method of claim 1, wherein all of the hydrogen required to produce the bio-derived feedstock in the at least one hydrodeoxygenation reactor unit is provided from the at least one aromatization reactor unit.

14. The method of claim 1, wherein the aromatic hydrocarbon is benzene, and at least about 10 weight percent of the benzene is made from the biomass.

15. A reactor system for producing aromatic hydrocarbons comprising:
   a) a first feed pipe for supplying a first feed stream comprising naphtha;
   b) a second feed pipe for supplying a second feed stream comprising a bio-derived feedstock comprising paraffinic, naphthenic, and olefinic hydrocarbons, in which the second feed pipe combines with the first feed pipe to form a reactant stream pipe;
   c) a separation unit having an inlet and an outlet, situated in line with the first feed pipe, the second feed pipe, or the reactant stream pipe, configured to receive, respectively, the first feed stream, the second feed stream, or the reactant stream, and to discharge, respectively, a purified first feed stream, a purified second feed stream, or a purified reactant stream;
   d) an at least one aromatization reactor unit having an inlet to accept the reactant stream or the purified reactant stream, and further comprising an aromatization catalyst bed which converts at least a portion of the bio-derived feedstock to one or more aromatic hydrocarbons and hydrogen; and
   e) a biomass reactor unit located proximate to the at least one aromatization reactor unit which supplies the second feed stream comprising a bio-derived feedstock to the second feed pipe,
   wherein the hydrodeoxygenation reactor unit comprises an inlet configured to accept a starting material selected from cellulose, sugars, starch, lignocellulose, hemicellulose, lignin, or combinations thereof; and further comprises an outlet for discharging to the bio-derived feedstock to the second feed pipe.

16. A reactor system for producing aromatic hydrocarbons from a renewable source, the system comprising:
   a) at least one hydrodeoxygenation reactor unit comprising a first inlet for supplying a reactant stream comprising a biomass, a second inlet for supplying hydrogen, a hydrodeoxygenation catalyst bed, and an outlet for discharging a bio-derived feedstock into a first transfer pipe;
   b) at least one aromatization reactor unit proximate to the at least one hydrodeoxygenation reactor, comprising an inlet for supplying a reactant stream comprising the bio-derived feedstock from the first transfer pipe and naphtha from a second transfer pipe, an aromatization catalyst bed, and an outlet for discharging a reactor effluent stream comprising one or more aromatic hydrocarbons and hydrogen;
   c) a separation system for separating the reactor effluent into one or more aromatic hydrocarbons, hydrogen, and a raffinate; and
   d) a third transfer pipe for supplying the hydrogen from the separation system to the second inlet of the hydrodeoxygenation reactor unit,
   wherein the biomass comprises cellulose, sugars, starch, lignocellulose, hemicellulose, lignin, or combinations thereof.

17. The reactor system of claim 16, wherein the bio-derived feedstock comprises hexane and the one or more aromatic hydrocarbons comprises benzene.

18. The reactor system of claim 16, wherein the hydrodeoxygenation catalyst bed comprises an acidic catalyst; a catalyst based on molybdenum, rhenium, iron, ruthenium, osmium, cobalt, rhodium, iridium, nickel, palladium, or platinum; an Ir—Re catalyst; or a ZSM-5 zeolite.

19. The reactor system of claim 16, wherein the aromatization catalyst comprises an inorganic support, a Group 8-10 metal, and one or more halides.

20. The reactor system of claim 19, wherein the inorganic support is selected from one or more of silica, alumina, a zeolite, clays, titania, magnesium oxide, or combinations thereof and wherein the aromatization catalyst comprises an inorganic support, a metal selected from platinum, Pt/Sn or Pt/Re, and one or more halides.

21. The reactor system of claim 20, wherein the zeolite is selected from L-zeolite, zeolite X, zeolite Y, omega zeolite, beta zeolite, ZSM-4, ZSM-5, ZSM-10, ZSM-12, ZSM-20, REY, USY, RE-USY, LZ-210, LZ-210-A, LZ-210-M, LZ-210-T, SSZ-24, SSZ-26, SSZ-31, SSZ-33, SSZ-35, SSZ-37, SSZ-41, SSZ-42, SSZ-44, MCM-58, mordenite, mazzite, faujasite, or combinations thereof.

22. The method of claim 14, further comprising:
   contacting the benzene with ethylene under conditions to produce ethylbenzene; and
   dehydrogenating the ethylbenzene to produce a styrene product.

23. A method for producing renewable styrene comprising:
   a) contacting a biomass with hydrogen in the presence of a hydrodeoxygenation catalyst in at least one hydrodeoxygenation reactor unit, under conditions that produce bio-derived feedstocks comprising hexanes;
   b) introducing the bio-derived feedstocks in combination with a naphtha reactant stream into at least one aromatization reactor unit and contacting the bio-derived feedstocks and naphtha with an aromatization catalyst under conditions that produce benzene and hydrogen;
   c) providing at least a portion of the hydrogen produced in the at least one aromatization reactor unit to the at least one hydrodeoxygenation reactor unit for contacting the biomass;
   d) contacting the benzene with ethylene under conditions to produce ethylbenzene, wherein the benzene comprises at least about 10 wt. % bio-derived benzene; and
   e) dehydrogenating the ethylbenzene to produce a styrene product,
   wherein the biomass comprises cellulose, sugars, starch, lignocellulose, hemicellulose, lignin, or combinations thereof.

24. The method of claim 1, wherein the biomass is wood.

25. The method of claim 23, wherein the biomass is wood.

* * * * *